United States Patent
Yamamoto

[11] Patent Number: 5,905,563
[45] Date of Patent: May 18, 1999

[54] BLINK DETECTION FACE IMAGE PROCESSING APPARATUS UTILIZING RETINAL REFLECTION IMAGE

[75] Inventor: Takayuki Yamamoto, Tokyo, Japan

[73] Assignee: Mitsubishi Denki Kabushiki Kaisha, Tokyo, Japan

[21] Appl. No.: 09/008,294

[22] Filed: Jan. 16, 1998

[30] Foreign Application Priority Data

Oct. 2, 1997 [JP] Japan .................................. 9-269595

[51] Int. Cl.$^6$ ...................................................... A61B 3/00
[52] U.S. Cl. ............................................................ 351/210
[58] Field of Search .................................... 351/205, 206, 351/207, 208, 209, 210, 212, 246

[56] References Cited

U.S. PATENT DOCUMENTS

| | | | |
|---|---|---|---|
| 4,838,681 | 6/1989 | Pavlidis .................................... | 351/210 |
| 4,973,148 | 11/1990 | Hutchinson ............................. | 351/210 |
| 5,220,360 | 6/1993 | Verdooner et al. ..................... | 351/212 |

FOREIGN PATENT DOCUMENTS

| | | |
|---|---|---|
| 9-44680 | 2/1997 | Japan . |
| 9-198508 | 7/1997 | Japan . |

*Primary Examiner*—George Manuel
*Attorney, Agent, or Firm*—Sughrue, Mion, Zinn, Macpeak & Seas, PLLC

[57] ABSTRACT

A face image processing apparatus is adapted to extract a retinal reflection image accurately and decide the opened and closed states of eyes correctly, regardless of reflection images of eyeglasses, which exist around the retinal reflection image. The face image processing apparatus includes a lighting unit 11 for irradiating a face of a person 1 to be detected, a photographing unit 10 for photographing a face image of the detected person 1, a binarization unit 21 for binarizing a variable-density (light and shade) image, a feature extracting unit 23 for extracting binarized white pixel regions, and an eye-state decision unit 24 for deciding the eye states of the detected person 1. The feature extracting unit 23 sets the most of entire white pixel regions as the retinal reflection image candidate regions, distinguishes and extracts the retinal reflection images and the reflection images according to an attribute of a previous screen by a correlation of the present screen candidates and the previous screen candidates, whereby a false detection of the reflection images can be prevented. At the same time, the feature extracting unit 23 creates the retinal reflection image candidates according to the relative positional relation of the left and right eyes, thereby extracting the retinal reflection images accurately through complementation of these two extractions, regardless of the reflection images such as the eye glasses which might exist around the retinal reflection images.

10 Claims, 18 Drawing Sheets

SCREEN RANGE (a)

SCREEN RANGE (b)

FIG. 8
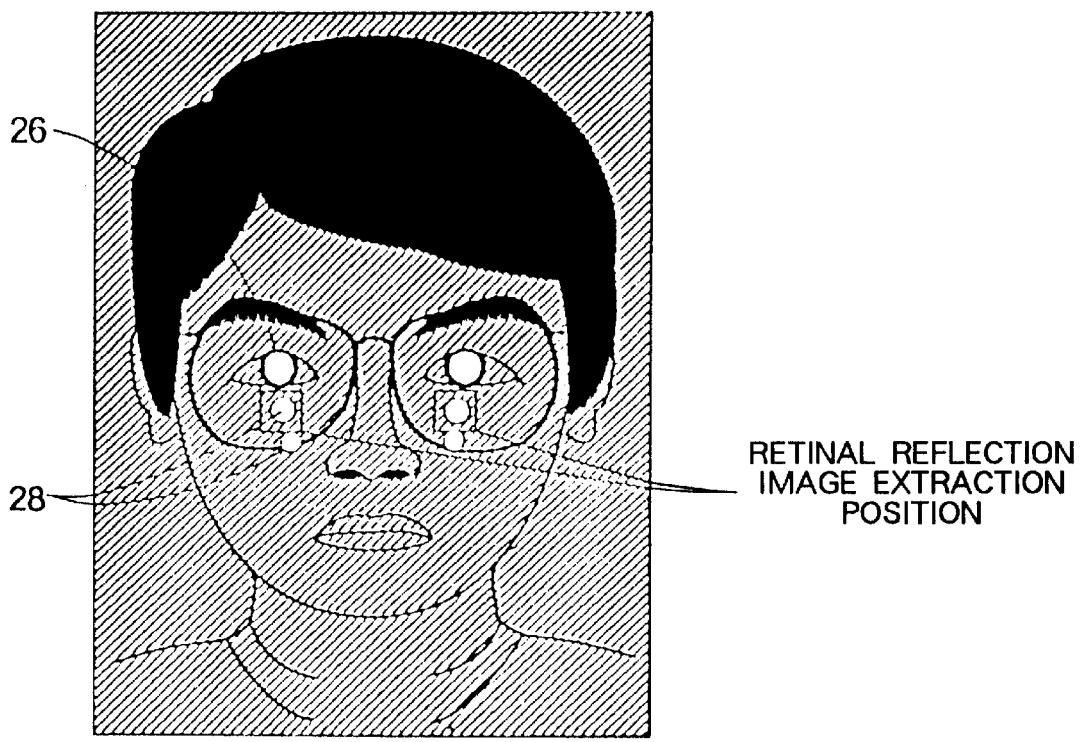
RETINAL REFLECTION
IMAGE EXTRACTION
POSITION
FIG. 9(a)
RIGHT EYE
TRACKING
WINDOW
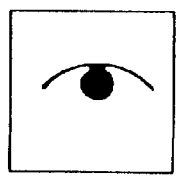
LEFT EYE
TRACKING
WINDOW
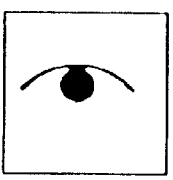
FIG. 9(b)
BOTH EYES
TRACKING
WINDOW
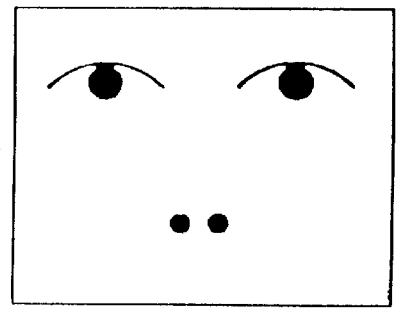

EXAMPLE OF CORRELATION
(n, nb), (n', nb')

FIG. 12(a)

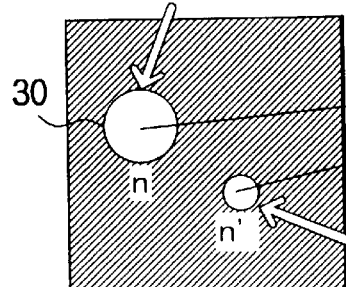

(3) SELECTION OF SMALLER AREA DIFFERENCE BETWEEN PRESENT AND PREVIOUS SCREENS (1) COORDINATION WITH PREVIOUS SCREEN (4) CONFLICT EXCLUSION

PRESENT SCREEN
n, n' : CANDIDATES OF PRESENT SCREEN

FIG. 12(b)

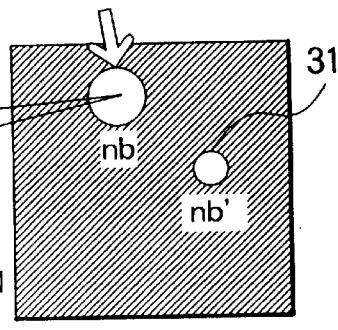

(2) CORRELATION OVERLAP

PREVIOUS SCREEN
nb, nb' : CANDIDATES OF PREVIOUS SCREEN

FIG. 13(a)

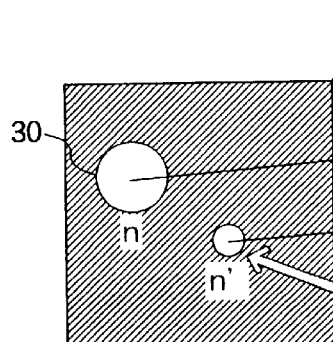

PRESENT SCREEN
n, n' : CANDIDATES OF PRESENT SCREEN

FIG. 13(b)

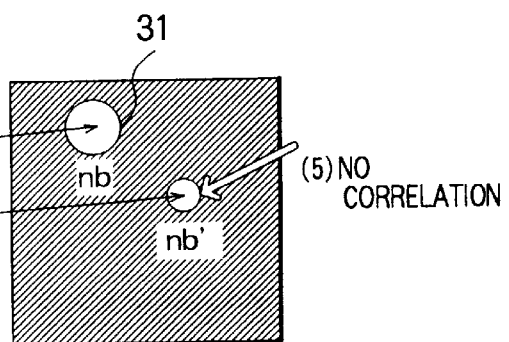

(1) CORRELATION WITH PREVIOUS SCREEN (5) NO CORRELATION (6) NEW CORRELATION

PREVIOUS SCREEN
nb, nb' : CANDIDATES OF PREVIOUS SCREEN (7) RESTRATION FROM CONFLICT EXCLUSION

FIG. 18

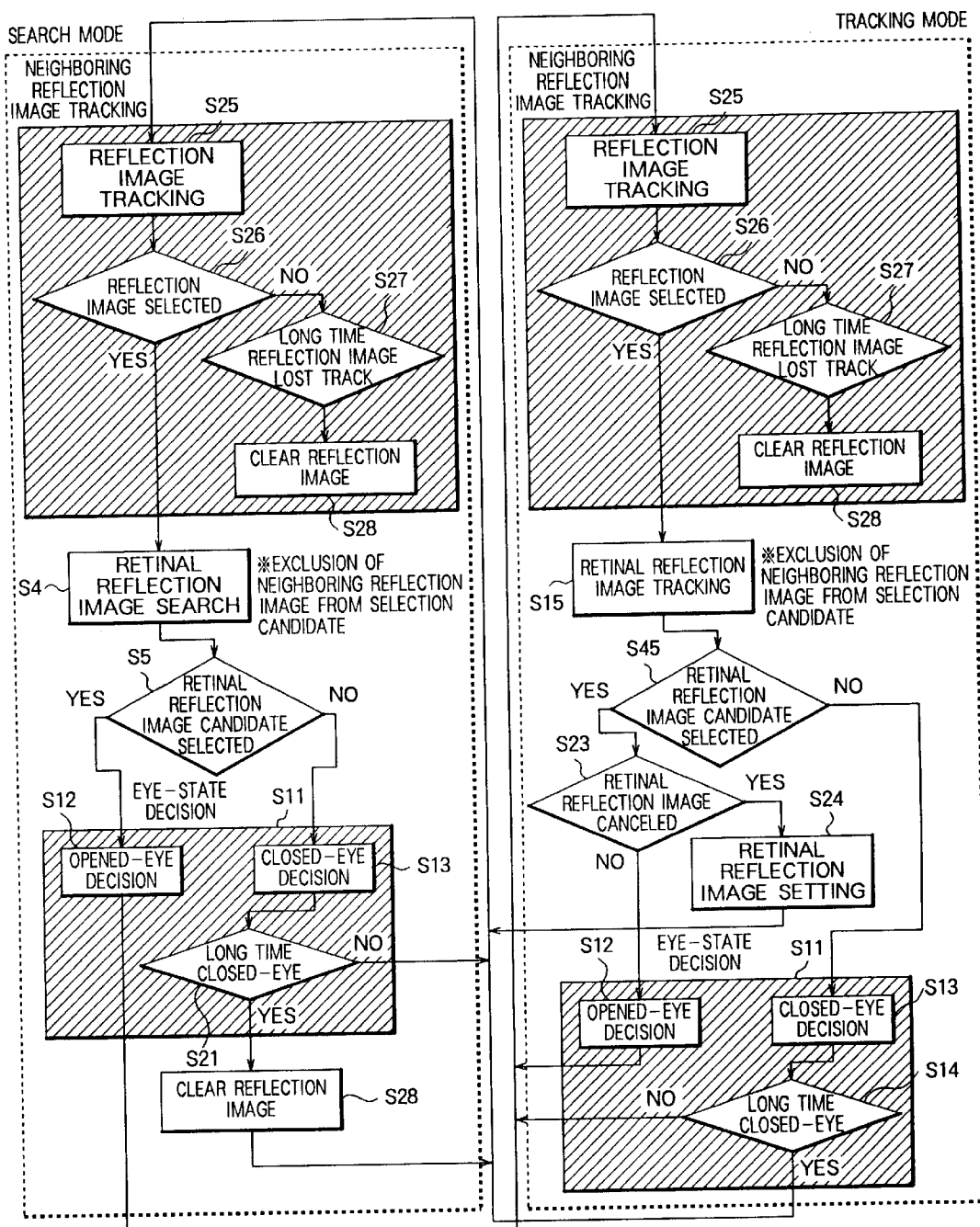

※THERE IS NO NEIGHBORING REFLECTION IMAGE SEARCH, AND REFLECTION IMAGE SETTING IS IMPLEMENTED ONLY BY EXCHANGE WITH RETINAL REFLECTION IMAGE.
※EVEN IF LOSING NEIGHBORING REFLECTION IMAGE DURING TRACKING, CANCEL POSITION (REF IMAGE) IS VALID UNTIL CLEARING IT.
※FOR NEGHBORING REFLECTION IMAGE, THERE IS A RESTORATION PROCESS FROM A LOST TRACK BY ONE SIDE REFLECTION IMAGE TRACKING.

36 BINARIZATION THRESHOLD VALUE DECREASING PROCESS
37 BINARIZATION THRESHOLD VALUE INCREASING PROCESS

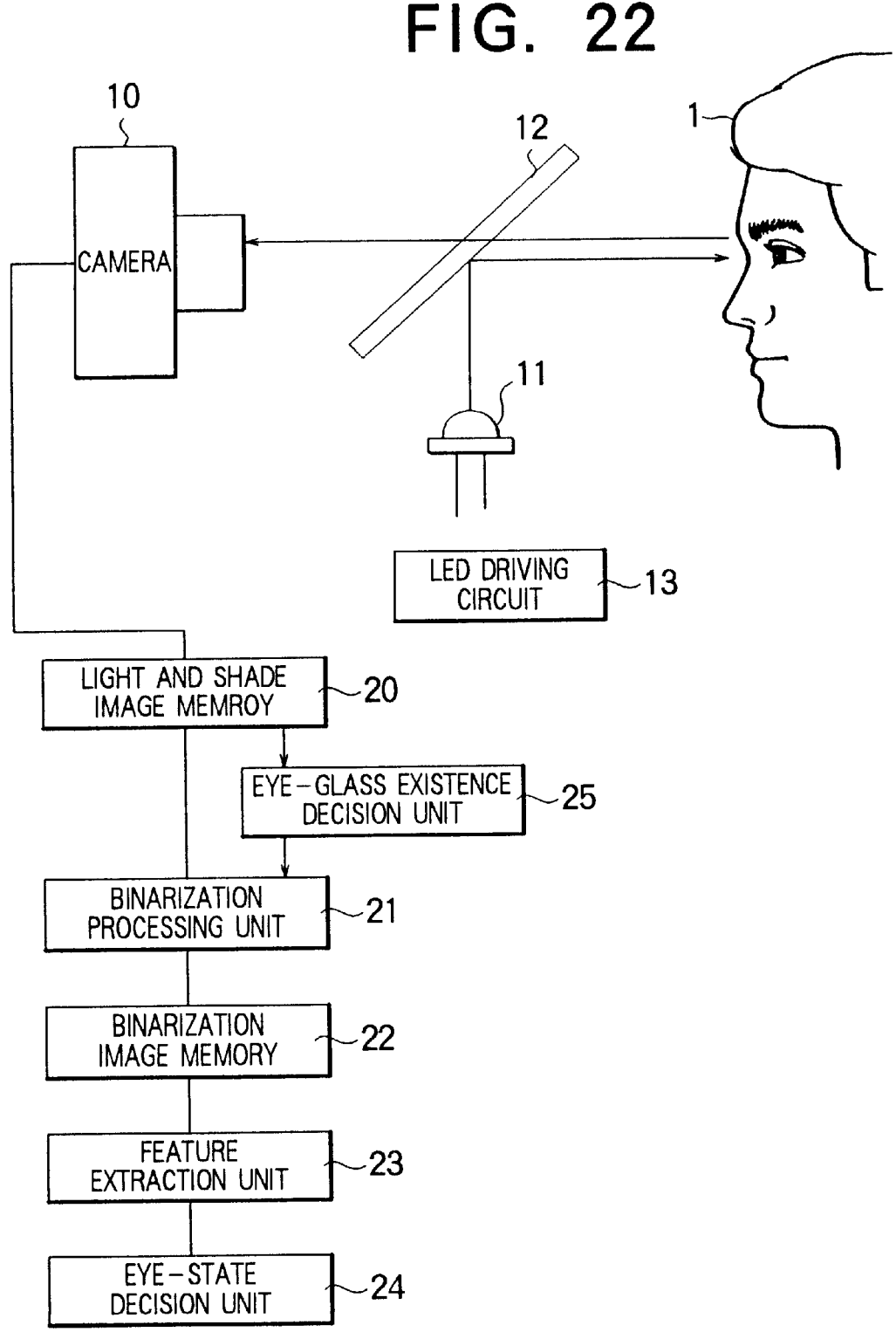

BLINK DETECTION FACE IMAGE PROCESSING APPARATUS UTILIZING RETINAL REFLECTION IMAGE

BACKGROUND OF THE INVENTION

1. Field of the Invention

The present invention relates to a face image processing apparatus having means for distinguishing a retinal reflection image from other reflection images using an image processing, for extracting it, and for deciding an eye-state (i.e., opened or closed eye) according to an existing state of the retinal reflection image.

2. Description of the Related Art

One example of such a face image processing apparatus is described in Japanese Patent Application No. 8-5713 filed on Jan. 17, 1996 and assigned to the same assignee. This face image processing apparatus is principally aimed at removing a reflection image at a stage of setting a retinal reflection image candidate region within a binarized image. As conditions for setting a candidate region, a shape characteristic and a mobility vector from a previous screen are used. Also, the apparatus is featured in the provision of a retinal reflection image region extraction means for extracting the left-side and right side retinal reflection images, separately.

FIG. 22 is a configuration diagram showing a stimulated-state or wakefulness detection apparatus disclosed in the above-mentioned Japanese Patent Application No. 8-5713. In this figure, a numeral 1 indicates a person to be detected (i.e., hereinafter simply referred to as a detection subjected person), a numeral 10 indicates a camera, a numeral 11 indicates a lighting unit in the form of an LED device, a numeral 12 indicates a half-mirror, a numeral 13 indicates a LED driving circuit, a numeral 20 indicates a variable-density (light and shade) image memory, a numeral 21 indicates a binarization means, a numeral 22 indicates a binarized image memory, a numeral 23 indicates a characteristics extraction means, a numeral 24 indicates an eye-state decision means, and a numeral 25 indicates an optical glass existence and/or non-existence decision means. With the above arrangement, light irradiated by the LED device 11 illuminates the face of the detection subjected person 1 through the half-mirror 12.

Photographing the face of the detection subjected person 1 by the camera 10, a pupil of the detection subjected person 1 is taken as if the pupil is flashing, as shown in FIG. 2(a), according to reflected light from a retina inside the eyeball. This is because the retina has a character of sending the reflected light back to the same direction as the incident light. Since the reflection image from this retina will be photographed remarkably brighter than other parts of the face, with a binarized process for the photographed light and shade image, an image region with a larger luminance could be extracted as a pupil region. By paying attention to a shape feature of this pupil region (retinal reflection image), the opened and closed states of the eyes can be decided.

FIG. 15 is a flowchart showing a retinal reflection image tracking algorithm of the aforementioned face image processing apparatus. At first, by controlling the camera 10, an output image from the camera 10 is adjusted to an appropriate brightness value (step S1). Next, by mode selection, either one of a search mode for extracting a retinal reflection image for the first time or at other times from a lost-eye state in which an eye is lost or not seen, or of a tracking mode for continuously tracking the retinal reflection image which is being currently in the progress of an extraction is selected (step S2).

In the search mode, setting a search window for the most of an entire face is set (step S3); a region to be a candidate of a retinal reflection image is selected according to a size/shape of the binarized region (step S4); and a retinal reflection image region is extracted from those candidates according to a relationship between the relative positions of the left and right eyes (step S5).

In the tracking mode, the tracking windows is set for tracking the retinal reflection image binarized regions found in the search mode, in the left and right, separately (step S6). Specifically, in order to track the left and right eyes separately, a left-eye tracking window (step S7) as well as a right-eye tracking window are set (step S8). Then, the left and right eye candidates are created in the tracking windows (step S4). That is, the left eye candidate in the left eye tracking window is created (step S9), and the right eye candidate in the right eye tracking window is created (step S10). Next, a retinal reflection image candidate from the left and right eye candidates is selected (step S5), and a decision of a closed eye is made (step S11). That is, if the retinal reflection image of either one of the left or the right could be extracted, then an opened-eye decision is made as an eye state (step S12), and a closed-eye decision is made if no retinal reflection image could be extracted (step S13). When the closed-eye decision continues for a long time (equal to or more than a predetermined time), then a lost-eye state is determined (step S14), and the process returns to the search mode for performing re-extraction once again from the beginning.

FIG. 2(a) represents an original image when the detection subjected person 1 is with the naked eyes, and FIG. 2(b) shows the binarized images thereof.

The above-mentioned face image processing apparatus could, as in FIGS. 2(a) and 2(b), extract the retinal reflection image binarized region 27 according to the shape characteristics such as a degree of squareness (i.e., ratio between side lengths of a rectangular shape) or an area thereof, because a reflection image other than the retinal reflection image 26 rarely appears, and thus could decide the opened and closed states of eyes, correctly.

FIG. 3(a) shows an original image when the detection subjected person 1 is with the eye glasses, and FIG. 3(b) shows the binarized images thereof.

The above-mentioned conventional face image processing apparatus could, as in the Japanese Patent Application 8-5713 Publication, even when the eye glass reflection images 28 exist, with paying attention to a point that a brightness is higher in the eye glass reflection image than in the retinal reflection image, distinguish the binarized regions 29 of the eye glass reflection images and the retinal reflection images, by making the binarized regions 29 to be doughnut shape as shown in FIG. 3(b) according to a binarized threshold value control, thus could extract the retinal reflection images.

Also, the reflection images are limited on the eye glass frame, and will not appear around the eyes.

Since the above-mentioned face image processing apparatus could remove the most of reflection images at a stage of extracting the retinal reflection image, the state with no candidate could be decided as the closed-eye state, finally.

As described above, in the above-mentioned face image processing apparatus, no reflection image other than the eye glass reflection images exist, and when the detection subjected person is with the naked eyes, the binarized images are only the retinal reflection images, and when wearing the eye glasses, the reflection images other than the retinal reflection images could be removed by the brightness difference.

However, with the above-mentioned face image processing apparatus, degradation of a relative resolution due to an expansion of the angle of field of the camera such as shown in FIGS. 4(a) and 4(b), or as in FIGS. 5(a) and 5(b), there were many false detection of the reflection images, since it can not distinguish the retinal reflection images 27 and the reflection images 29 other than them, for a change of a face image such as an appearance of a reflection image other than the eye glass reflection images due to an increased output of the LED.

Particularly, at a time of the closed eyes, the retinal reflection images 27 which have been tracked would disappear on the screen, so that there were instead many false detections of the reflection images 29 whose size/shape are very similar to the ones of retinal reflection images located around the eyes.

Once a false extraction is made, a correct position can not be extracted unless waiting for the next lost state of being seen, the eye-state decisions during that time would be much deviated from the actual opened and closed states of eyes, and thus an accurate eye-state decision can not be made.

SUMMARY OF THE INVENTION

The present invention is intended to solve the above-mentioned problems, and an object thereof is to provide a face image processing apparatus capable of correctly deciding the opened and closed states of eyes, by stably tracking a retinal reflection image, without making a false detection, even in the case of a closed eye, as far as an initial extraction is carried out correctly, though there exist many reflection images other than the retinal reflection images.

A face image processing apparatus according to the present invention comprises: a retinal reflection image creation optical means for creating retinal reflection images in eye balls of a person; an image input means for inputting a face image of the person; a binarization means for binarizing a light and shade image obtained by the image input means; a retinal reflection image candidate creation means for defining retinal reflection image candidate regions in a binarized image; a retinal reflection image region extraction means for extracting a retinal reflection image region from a group of the retinal reflection image candidate regions; and an eye-state decision means for deciding an opened or a closed eye according to an existing state of the retinal reflection image region extracted; wherein the retinal reflection image region extraction means comprises a retinal reflection image candidate region correlation extraction means for correlating a retinal reflection image candidate region of a present time with a retinal reflection image candidate region of a predetermined time before.

In a preferred form of the present invention, the retinal reflection image candidate creation means comprises a prohibiting region setting means for prohibiting a creation of a retinal reflection image candidate within a binarized image. The prohibiting region setting means sets, as the prohibiting regions for prohibiting the retinal reflection image candidate creation, the regions within the screen including the binarized regions which may be mistakenly decided as the retinal reflection images.

In a further preferred form of the present invention, the retinal reflection image candidate creation means comprises a left and right retinal reflection images simultaneous search region setting means for setting a region, for which a retinal reflection image candidate creation is implemented, to a range including the left and right retinal reflection images. That is, the left and right retinal reflection image simultaneous search region setting means sets the tracking window to a range including the left and right retinal reflection images, as in FIG. 9(b), by extending the afore-mentioned tracking window of FIG. 9(a) in the up and down directions of the face with the previous screen eye positions being taken as the starting points.

In a further preferred form of the present invention, the retinal reflection image candidate creation means comprises a retinal reflection image candidate region separation means for separating the retinal reflection image candidate regions neighboring or contacting with each other.

In a further preferred form of the present invention, the retinal reflection image candidate region correlation extraction means comprises a retinal reflection image candidate region correlation overlap selection means which selects, if a plurality of retinal reflection image candidate regions of the present time are overlappingly correlated with the same retinal reflection image candidate regions of the predetermined time before, one of the retinal reflection image candidate regions of the present time.

In a further preferred form of the present invention, the retinal reflection image candidate region correlation overlap selection means comprises a retinal reflection image candidate region conflict exclusion restoration means for renewing and correlating the retinal reflection image candidate regions of the present time, which have been excluded from the correlation with the same retinal reflection image candidate regions of the predetermined time before effected by the retinal reflection image candidate region correlation overlap selection means, with other retinal reflection image candidate regions of the predetermined time before. The retinal reflection image candidate region conflict exclusion restoration means will correlate the candidates conflicted and excluded in the previous overlap selection processing with candidate regions which if exist in the overlap selection processing, neighbor in the conflicted and excluded candidates in the previous screen and for which correlation has not yet been made.

In a further preferred form of the present invention, the retinal reflection image candidate region extraction means comprises a retinal reflection image decision means for evaluating the retinal reflection image candidate regions which are being extracted as the retinal reflection image at the present time, and for abolishing the retinal reflection image candidate regions which are being extracted as the retinal reflection image at the present time, in dependence upon a result of the evaluation. The retinal reflection image decision means decides from the opened- or closed-eye state as to whether the retinal reflection image extraction regions being tracked at present time are the retinal reflection images or the reflection images, and then abolishes the regions being now tracked by rewriting the attributes thereof.

In a further preferred form of the present invention, the retinal reflection image decision means further comprises a non-retinal reflection image region extraction means for continuously extracting, independent of the retinal reflection image regions, the retinal reflection image candidate regions which have been abolished as the non-retinal reflection images by the retinal reflection image decision means. The non-retinal reflection image region extraction means recognizes the regions which have been decided as the reflection images according to the retinal reflection image decision, as the retinal reflection image neighboring reflection images, and implements a continuous tracking independent of the retinal reflection images.

In a further preferred form of the present invention, the retinal reflection image extraction means comprises: a retinal reflection image relative position relation extraction means for extracting, to the left and right simultaneously, the retinal reflection image candidate regions of the present time as the left and right retinal reflection images; and a retinal reflection image region selection means for selecting one of two kinds of retinal reflection image regions extracted by the retinal reflection image candidate region correlation extraction means and the retinal reflection image relative position relation extraction means. The relative position relation extraction means extracts the retinal reflection image candidate regions based on the relative positional relation such as a degree of horizontal (levelness), a distance between both eyes and the like for establishing the left and right eyes as a pair. Further, the retinal reflection image region selection means selects one of the two candidates of the retinal reflection image correlation means and the relative position relation extraction means according to the existing situations thereof and the result of the above evaluation.

In a further preferred form of the present invention, the binarization means comprises a binarized threshold value control means for controlling a binarized threshold value corresponding to a size of a retinal reflection image.

The above and other objects, features and advantages of the present invention will more readily apparent from the following detailed description of preferred embodiments of the invention taken in conjunction with the accompanying drawings.

BRIEF DESCRIPTION OF THE DRAWINGS

FIG. 8 is an illustrative diagram showing an example of a retinal reflection image false detection according to a fourth embodiment of the present invention;

FIGS. 9(a) and 9(b) are illustrative diagrams showing a method of setting a tracking window according to the first embodiment of the present invention;

FIGS. 12(a) and 12(b) are illustrative diagrams showing an overlap processing at a time when having conflicted with a correlation in the retinal reflection image correlation extraction candidate according to the first embodiment of the present invention;

FIGS. 13(a) and 13(b) are illustrative diagrams showing a restoring processing of the candidates which have been removed through conflict upon correlation in the retinal reflection image correlation extraction candidate according to the first embodiment of the present invention;

FIG. 18 is a flowchart showing a retinal reflection image tracking algorithm according to the first embodiment of the present invention including the neighboring reflection image extraction processing according to the fourth embodiment of the present invention;

FIG. 22 is a configuration diagram simplifying the conventional face image processing apparatus.

DESCRIPTION OF THE PREFERRED EMBODIMENTS

In the following, embodiments of the present invention will be described in detail with reference to the accompanying drawings. In the meantime, in the figures, the identical numbers indicate the identical parts, and the regions 27, 29 indicate binarized white pixel regions.

FIRST EMBODIMENT

Figure 1:
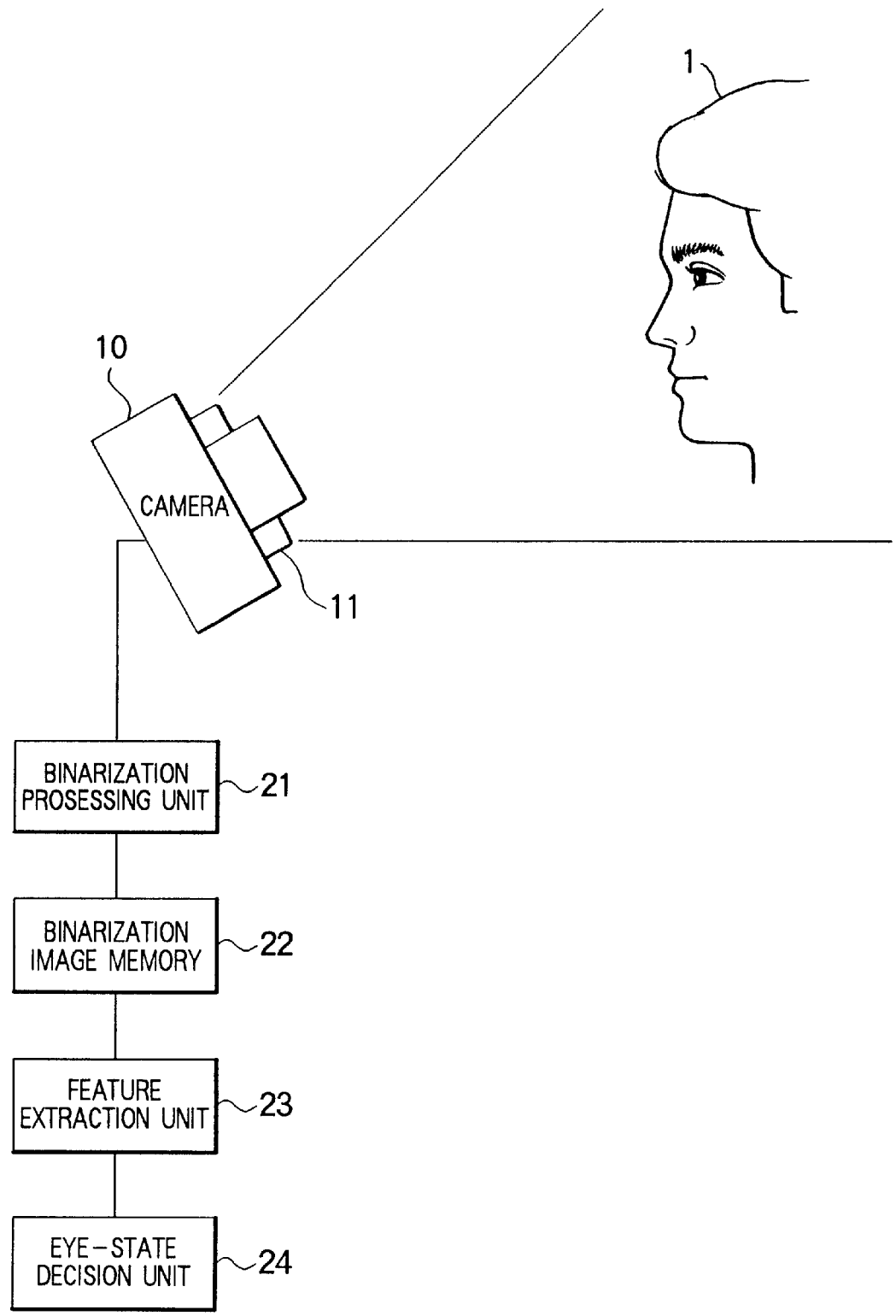
FIG. 1 is a configuration diagram simplifying a face image processing apparatus of a first embodiment of the present invention.
Figure 2A:
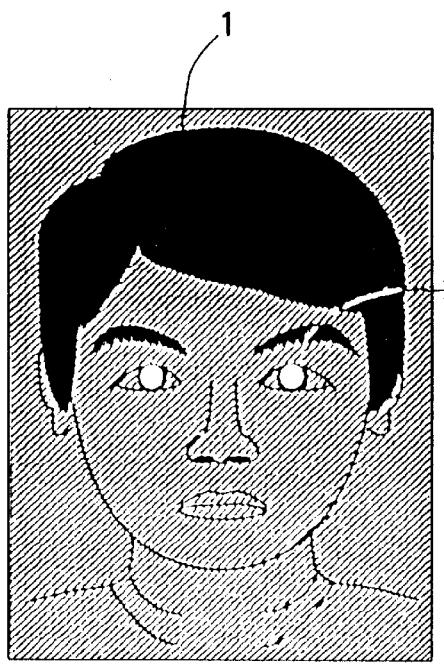
FIGS. 2(a) and 2(b) show a conventional face original image and a binarized image of a detection subjected person with the naked eyes.
Figure 2B:
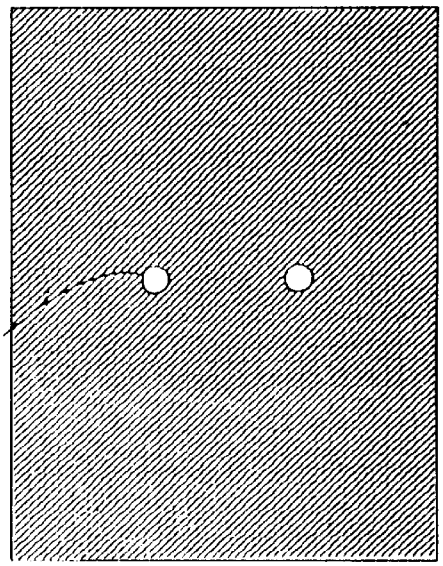
Figure 3A:
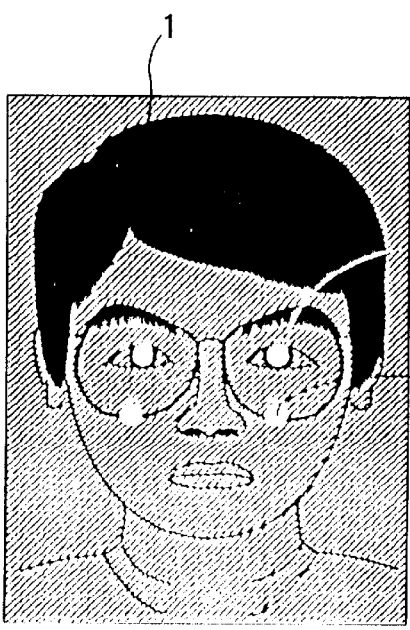
FIGS. 3(a) and 3(b) show a conventional face original image and a binarized image of a detection subjected person with the eye glasses.
Figure 3B:
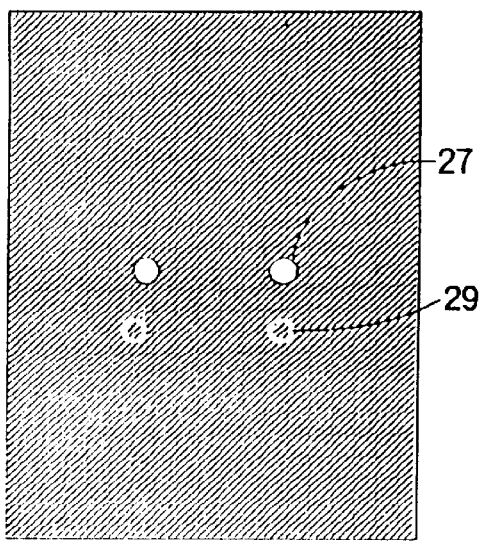
Figure 4A:
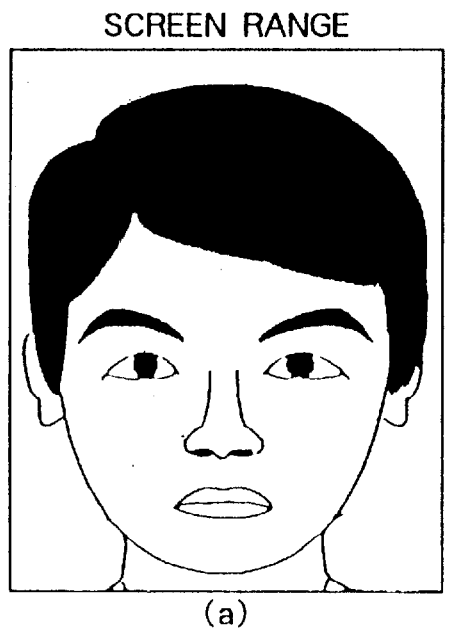
FIGS. 4(a) and 4(b) are illustrative diagrams showing an example of an expansion of the angle of field according to the first embodiment of the present invention.
Figure 4B:
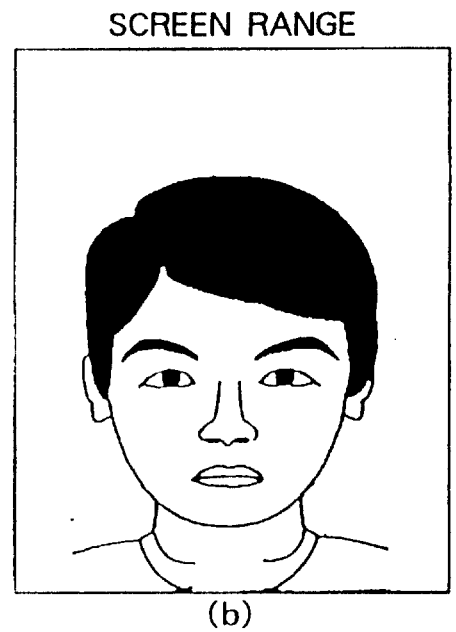
Figure 5A:
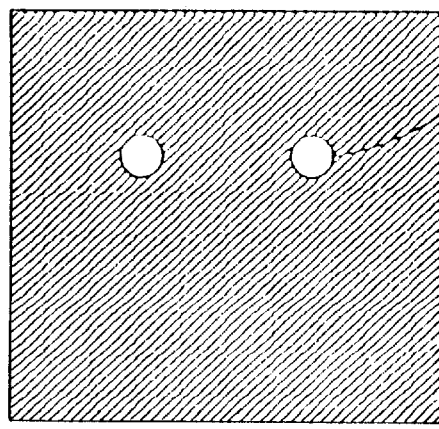
FIGS. 5(a) and 5(b) show a binarized image of a reflection image by a LED light according to the first embodiment of the present invention.
Figure 5B:
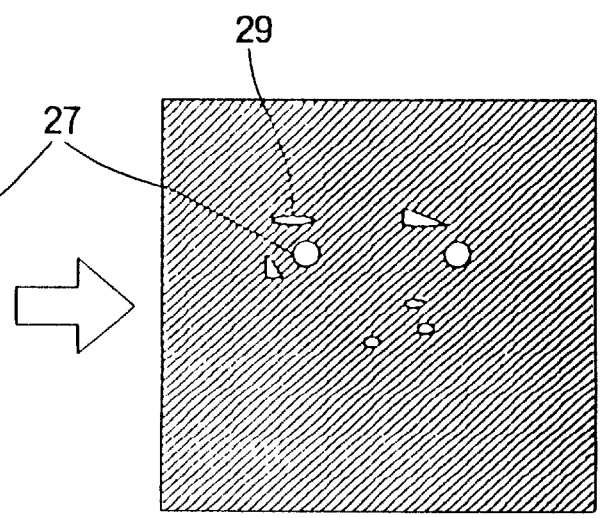

FIG. 1 is a configuration diagram of a face image processing apparatus of a first embodiment of the present invention. In FIG. 1, a numeral 1 indicates a face of a person to be detected, a numeral 10 indicates an image input or photographing means in the form of a CCD camera for photographing and inputting a face image of the detection subjected person, a numeral 11 indicates a lighting means in the form of a LED device for irradiating the face of the detection subjected person, and these components are the same as the above-mentioned conventional example. Further, a numeral 21 indicates a binarization unit for binarizing an image signal outputted from the CCD camera 10, a numeral 22 indicates a binary image memory for temporarily storing the binarized image outputted from the binarization unit 21, a numeral 23 indicates a feature extraction unit for inputting an image from the binary image memory 22 and for extracting white pixel regions, and a numeral 24 indicates an eye-state decision unit for deciding a retinal reflection image that is an opened- or closed-eye state from the feature extraction unit 23. The binarization unit 21, the feature extraction unit 23 and the eye-state decision unit 24 are implemented in software by a microcomputer and the like. Particularly, the first embodiment relates to the feature extraction unit 23.

Figure 21:
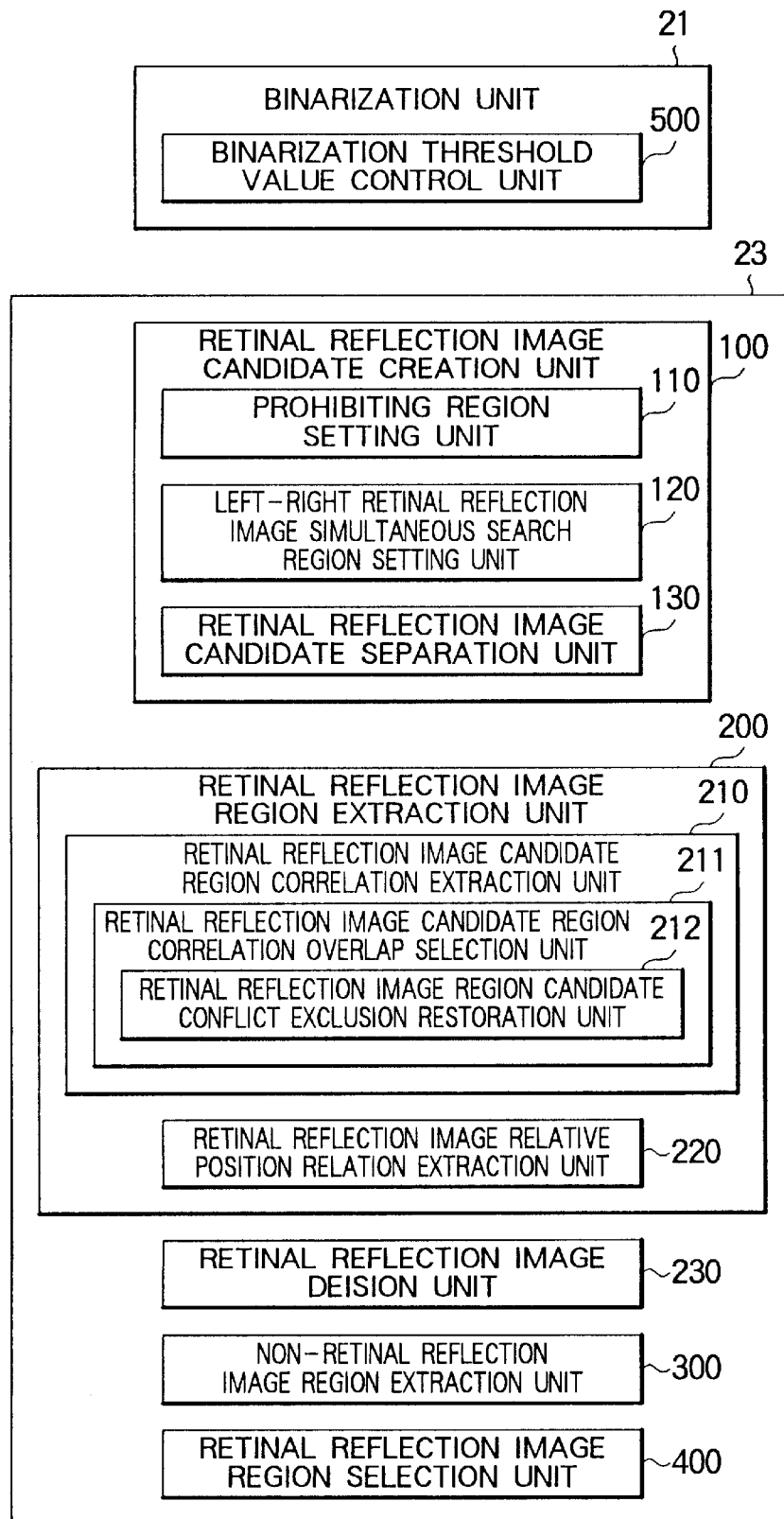
FIG. 21 is a functional block diagram showing the configurations of the binarization means and the feature extraction means according to the present invention.

As shown in FIG. 21, the feature extraction unit 23 comprises a retinal image candidate creation unit 100 for defining retinal reflection image candidate regions in the binarized image, a retinal reflection image region extraction unit 200 for extracting the retinal reflection image region from a group of the retinal reflection image candidate regions.

The retinal reflection image candidate creation unit 100 comprises a Prohibiting region setting unit 110 for prohibiting a retinal reflection image candidate creation within the binarized image, a left and right retinal reflection images simultaneous search region setting unit 120 for setting a region for which a retinal reflection image candidate creation is implemented, to a range including the retinal reflection images of the left and right, and a retinal reflection image candidate region separation unit 130 for separating the retinal reflection image candidate regions neighboring or contacting with each other.

The retinal reflection image region extraction unit 200 comprises a retinal reflection image candidate region correlation extraction unit 210 for correlating a retinal reflection image candidate region of a present time with a retinal reflection image candidate region of a predetermined time before, a retinal reflection image relative position relation extraction unit 220 for extracting, to the left and right simultaneously, the retinal reflection image candidate regions of the present time as the left and right retinal reflection images, and a retinal reflection image decision unit 230 for evaluating the retinal reflection image candidate regions in the progress of an extraction as the retinal reflection image at the present time, and for abolishing the retinal reflection image candidate regions in the progress of an extraction as the retinal reflection image at the present time in response to a result of the evaluation.

The retinal reflection image candidate region correlation extraction unit 210 comprises a retinal reflection image candidate region correlation overlap selection unit 211 for selecting any of the retinal reflection image candidate regions of the present time, at a time when a plurality of the retinal reflection image candidate regions of the present time are overlappingly associated or correlated with the same retinal reflection image candidate regions of the predetermined time before, and the retinal reflection image candidate region correlation overlap selection unit 211 comprises a retinal reflection image candidate region conflict exclusion return unit 212 for renewing and correlating the retinal reflection image candidate regions of the present time of which the retinal reflection image candidate region of the present time are excluded by overlappingly competing, to and with other retinal reflection image candidate regions of the predetermined time before.

Further, a feature extraction unit 23 comprises a non-retinal reflection image region extraction unit 300 for continuously extracting, independent of the retinal reflection image regions, the retinal reflection image candidate regions which have been abolished as the non-retinal reflection images by said retinal reflection image decision unit 230, and a retinal reflection image region selection unit 400 for selecting any of the two kinds of retinal reflection image regions extracted by the two kinds of retinal reflection extraction units of said retinal reflection image candidate region correlation extraction unit and retinal reflection image relative position relation extraction unit.

Also, the binarization unit 21 comprises a binarization threshold value control unit 500 for controlling a binarized threshold value corresponding to a size of a retinal reflection image.

Figure 16:
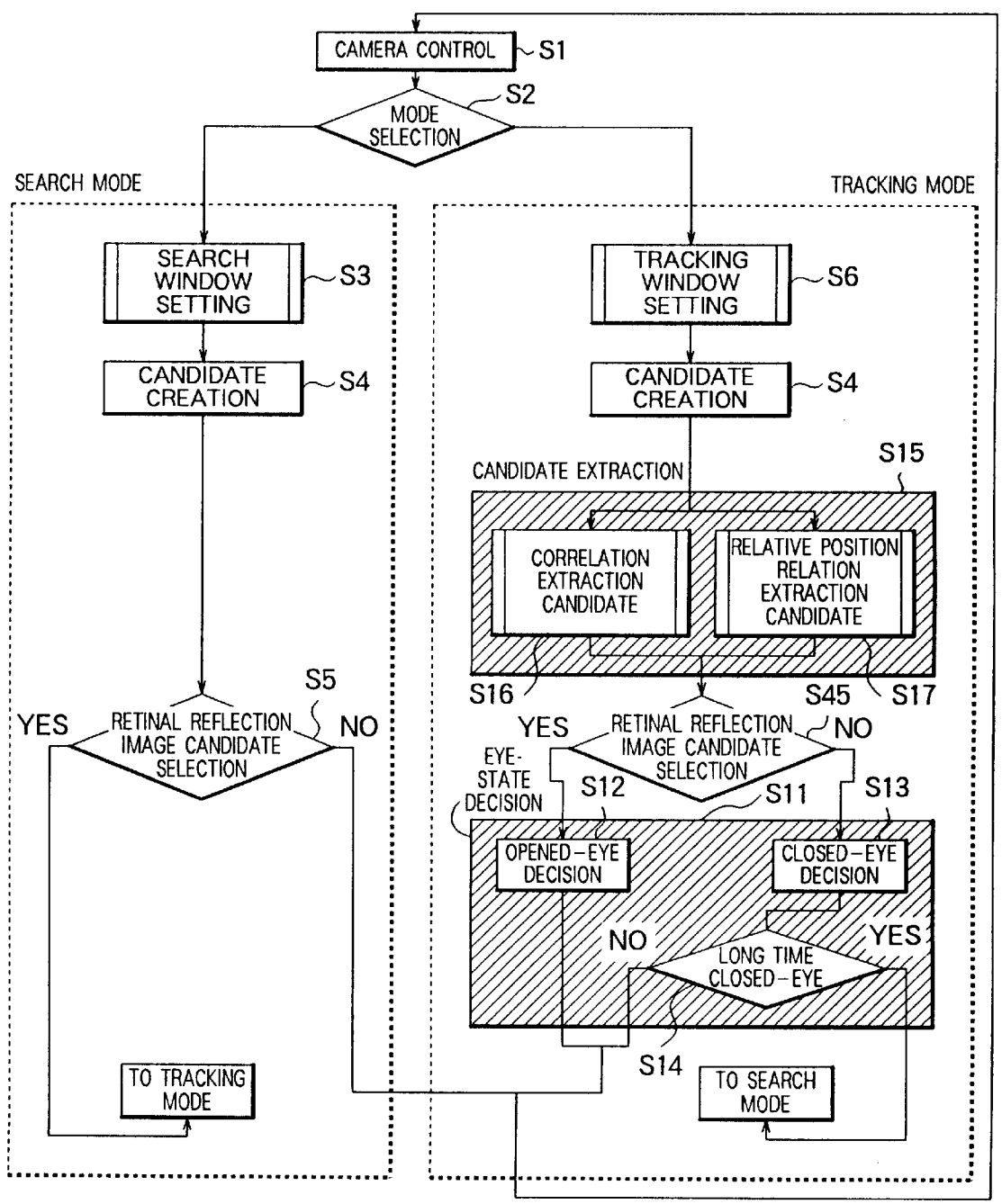
FIG. 16 is a flowchart showing a retinal reflection image tracking algorithm according to the first embodiment of the present invention.

FIG. 16 is a flowchart showing a retinal reflection image tracking algorithm according to the first embodiment of the present invention. Differing from the conventional example, in the tracking mode, the tracking windows including the retinal reflection images of the left and right shown in FIG. 9(b) is set (step S6), and the left and right eyes are basically treated as a pair. Further, two candidates of a correlation extraction candidate and a relative position relation candidate are created (step S15), and either one of two candidates thus created is selected (step S45).

Next, a method of creating the correlation extraction candidates of the step S16 will be described.

Figure 11:
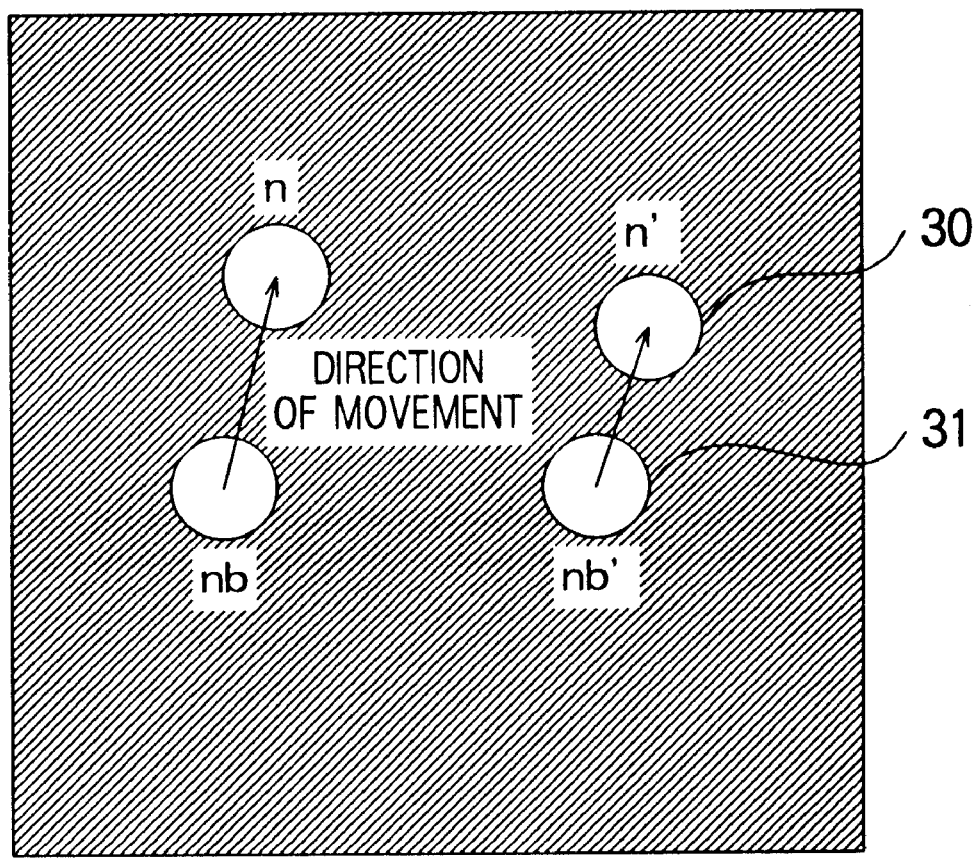
FIG. 11 is an illustrative diagram showing a correlation with a previous screen in a retinal reflection image correlation extraction candidate according to the first embodiment of the present invention.

Except the ones with extreme shapes, the most of entire white pixel regions are taken to be the retinal reflection image candidates, and as shown in FIG. 11, a difference from a previous screen position is taken as a reference, and then implementing a correlation as "he previous screen candidate 31 shifts to the present screen candidate 30 at the next screen".

For example, in FIG. 11, when the present screen candidate n is correlated as the same candidate with the previous screen candidate nb in time sequentially, by taking over an attribute in a previous screen, such that if the nb is the retinal reflection image then the n will take over an attribute of the retinal reflection image, and if the nb is the reflection image then the n will take over an attribute of the reflection image, an attribute of whether that candidate in the present screen is a retinal reflection image or a reflection image other than that one, is determined.

Although not being existed in the previous screen, an attribute of a new participation is given to the candidate existing in the present screen that is a newly appeared candidate in the present screen.

An attribute at a first time gives an attribute as the retinal reflection image at a time of extracting the retinal reflection image and gives an attribute as the reflection image other than that, and it is assumed of continuing those attributions, thereafter.

The attributes are by a continuation from a previous screen, except "the new participation", and not being newly set for each screen.

When having overlapped in the correlation, selecting the ones whose difference of an area with a previous screen is smaller in accordance with the procedures of (1) to (4) shown in FIGS. 12(a) and 12(b), and the one hand which was not selected is given of an attribute of "conflict exclusion" and is taken as a candidate which is not correlated separately from the new participation.

The above described attributes of the candidates are listed in Table 1.

TABLE 1

| Correlation Attributes (First Embodiment) | |
|---|---|
| Attribute | Setting Period of Time |
| Left retinal reflection image | Initial |
| Right retinal reflection image | Initial |

TABLE 1-continued

Correlation Attributes (First Embodiment)

| Attribute | Setting Period of Time |
| --- | --- |
| Reflection image correlated with Previous screen | Initial |
| Region newly appeared in Present screen but not existed in Previous screen (New Participation) | Every screen |
| Candidates exclude with Overlap Selection Process (conflict exclusion) | At a time of overlap selection process |

The candidates which have conflict excluded are, as shown in FIGS. 13(a) and 13(b), when a candidate exists at the neighboring of "selected candidates" in the previous screen, and when that candidate is not correlated, then a restoration of the conflict exclusion is implemented by correlating that candidate with a candidate of the conflict exclusion in accordance with the procedures of (5) to (7).

Next, a method of creating the relative position relation extraction candidate of the step S17 in FIG. 16 will be described.

Figure 14:
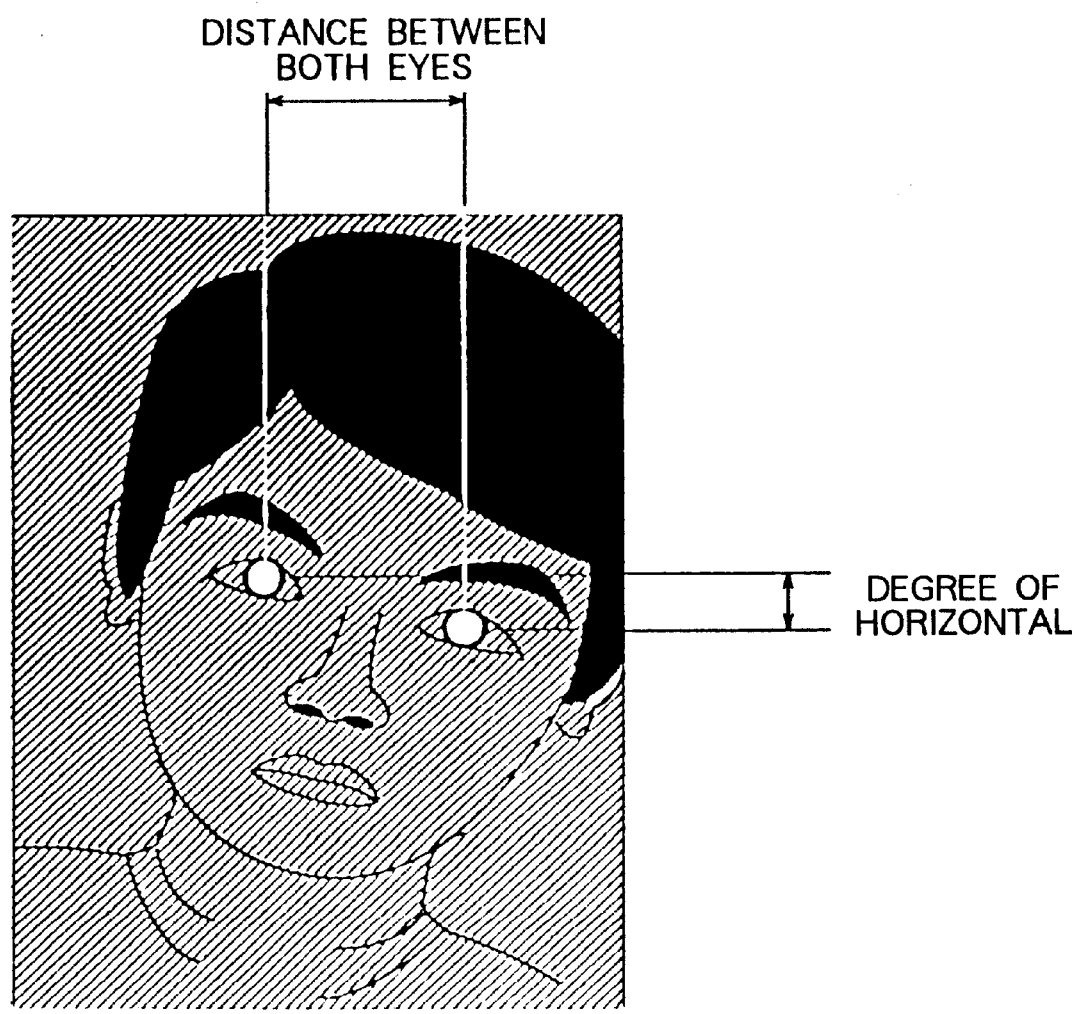
FIG. 14 is an illustrative diagram showing a horizontal degree or levelness and an eye-to-eye distance in the retinal reflection image relative position relation extraction candidate according to the first embodiment of the present invention.
Figure 15:
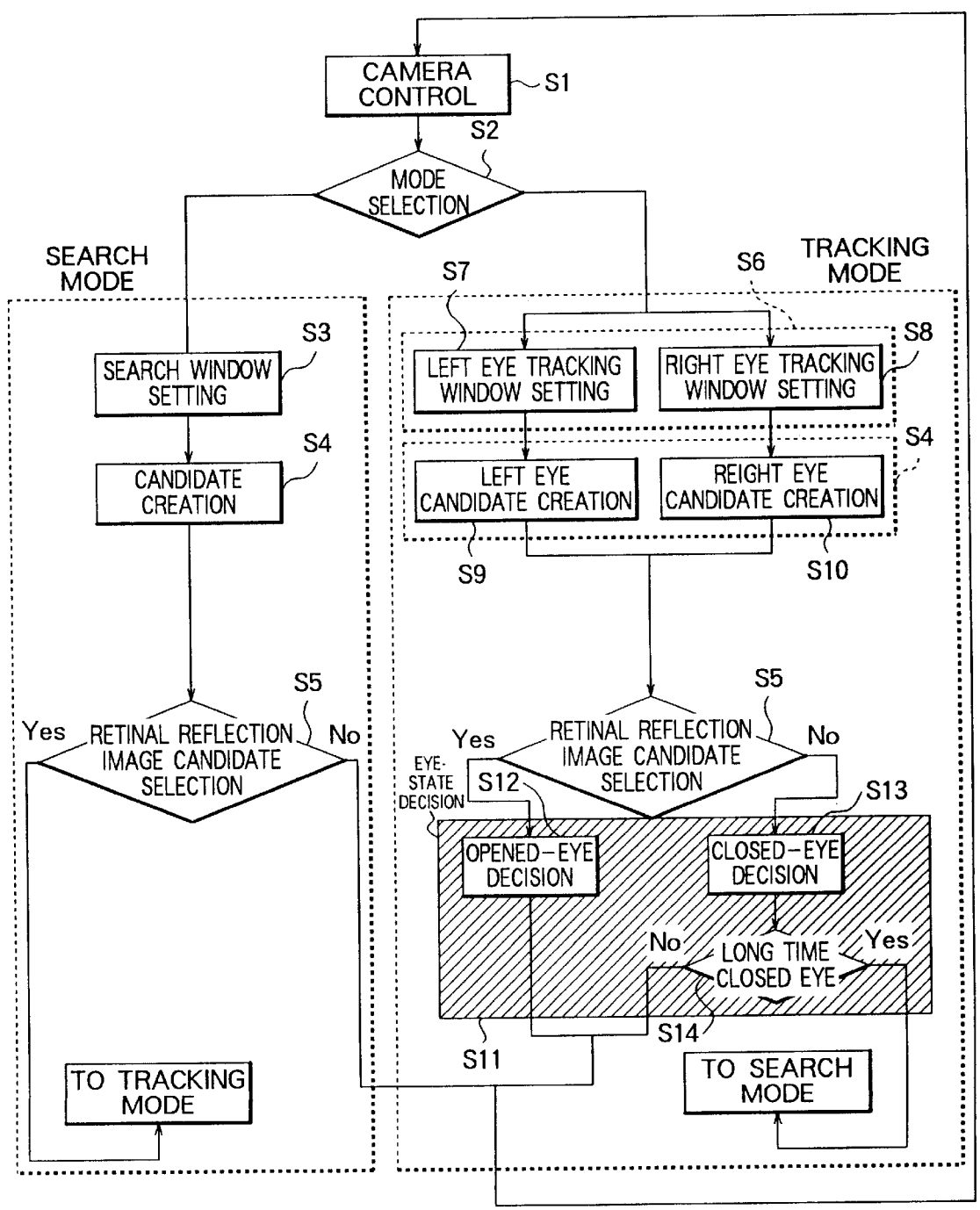
FIG. 15 is a flowchart showing a conventional retinal reflection image tracking algorithm.

The candidates to be recognized as the left and right eyes from the relative position relation of the left and right retinal reflection images, and for making a basis the relative positions of each other such as a degree of a horizontal (i.e., levelness)/a distance between the both eyes as shown in FIG. 14, it is absolutely created with the left and right pair.

Regardless of the previous screen position, a pair which are most matched with a condition of a relative position would be created.

Next, a candidate selection method for selecting any candidate from the two candidates will be described.

Assuming that the correlation extraction candidate of the step S16 in FIG. 16 has a precedence over the relative position relation extraction candidate of the step S17 in FIG. 16, and under the circumstances such as when it is difficult to immediately correlate a face movement, or at a time of a restoration of a retinal reflection image tracking from the closed eyes, or at a time of a restoration from an one eye tracking to both eyes tracking, although the retinal reflection images exist as the binarized regions, the correlation extraction candidates are not created, so that it is complemented by the relative position relation extraction candidate.

Also it is assumed that the one eye tracking is implemented by the correlation extraction candidate only.

Figure 19:
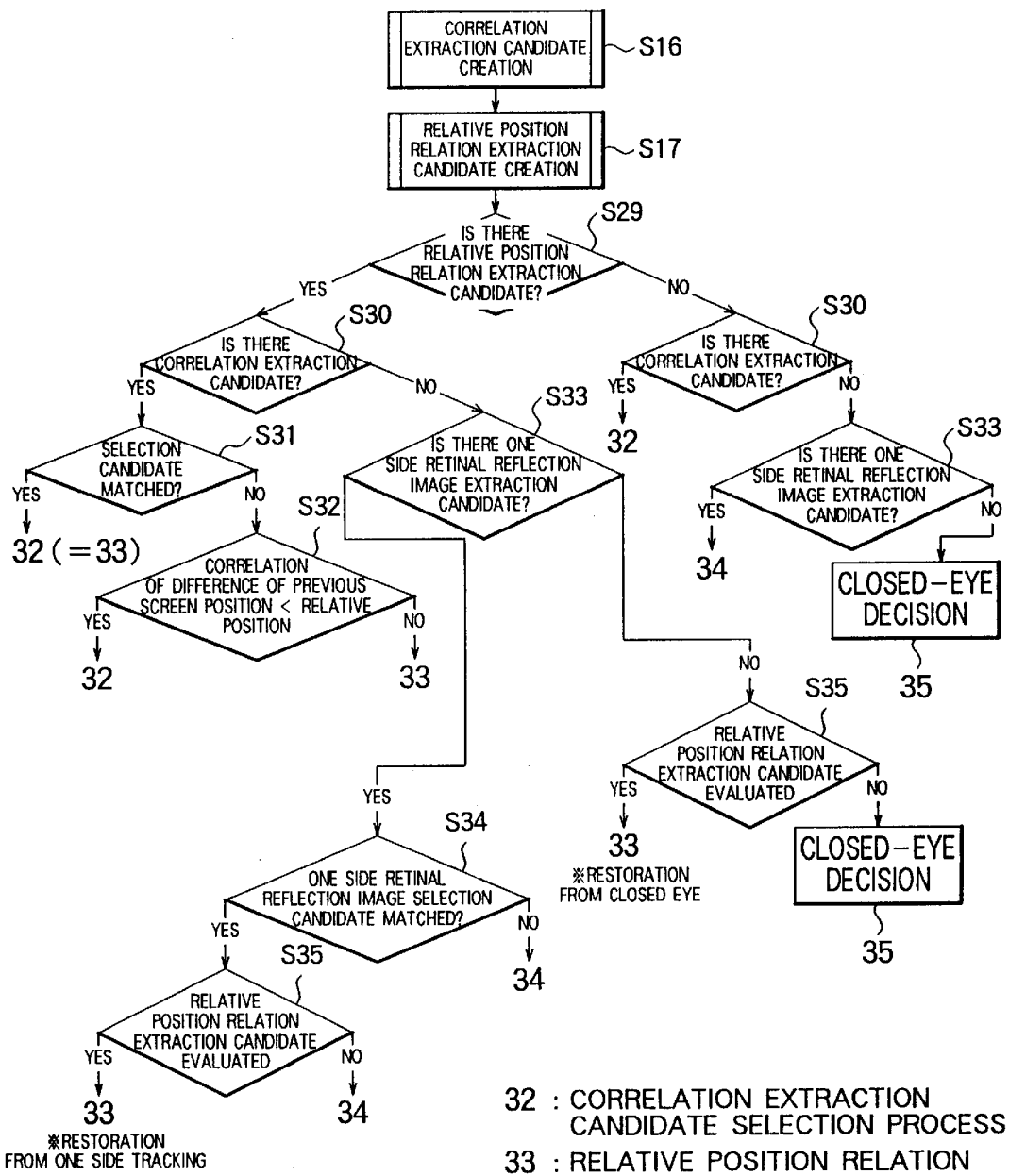
FIG. 19 is a flowchart showing a method of selecting a retinal reflection image candidate according to the first embodiment of the present invention.

From the creation states and the evaluation results of the correlation extraction candidates and the relative position relation extraction candidates, for example, a candidate is selected in accordance with the flowchart of the retinal reflection image candidate selection unit shown in FIG. 19.

As shown in FIG. 19, in the above-mentioned candidate selection unit, when both of a pair of the relative position relation extraction candidate (step S29) and the correlation extraction candidate (step S30) exist, and both of the selected candidates are not matched (step S31), the one with a smaller difference of the previous screen position is to be selected (step S32).

As shown in FIG. 19, at a time when selecting the above-mentioned relative position relation extraction candidate, it is to comprise the relative position relation extraction candidate evaluation step S35 which evaluates whether or not it is selectable according to a range of motion from the previous screen position and an attribute of the previous screen and the like.

As shown in FIG. 19, a restoration or return from an one eye tracking to both eyes tracking (step S33) is implemented when one of the correlation extraction candidates and one of the relative position relation extraction candidates are matched (step S34), and when the relative position relation extraction candidate is selected, according to an evaluation result of the other one of the relative position relation extraction candidates (step S35).

As shown in FIG. 19, a return of both eyes tracking from the closed eye is implemented when no correlation extraction candidate exist at the steps S30 and S33, and when the relative position relation extraction candidate is selected according to the evaluation result of the relative position relation extraction candidate at the step S35.

As an exception, it is implemented when returning from the lost-eye state to the search mode, and extracting the retinal reflection image.

As shown in FIG. 19, when the correlation extraction candidates are not a pair at the step S30, only one of the correlation extraction candidates exists at the step S33, and only when no relative position relation extraction candidate exists at the step S29, or only when the relative position relation extraction candidates are not selected according to the evaluation result at the step S34 or S35, it would be as the one eye tracking 34. Therefore, the one eye tracking 34 is implemented by only the above-mentioned retinal reflection correlation unit.

As shown in FIG. 19, when no correlation extraction candidate exists at the steps S30, S33, and no relative position relation extraction candidate exists at the step S29, or when the relative position relation extraction candidates do not fulfill the conditions as a result of the evaluation at the step S35, it would be as the closed eye decision 35.

In this first embodiment, for the correlation extraction candidates, the correlation was implemented by using the position information of the previous screen only, but it could be considered to use the position information of the one which is further back time sequentially, such as one more previous than the previous screen.

In the face image processing apparatus according to the first embodiment, since for the most of entire binarized regions, tracking is performed with the attributes being determined, the retinal reflection image can be extracted accurately regardless of an existence of a reflection image, and hence the opened and closed states of the eyes can be decided correctly.

SECOND EMBODIMENT

This second embodiment is the one which adds a setting of a prohibiting region in the tracking window setting of the above-mentioned first embodiment.

The prohibiting region setting will be described.

Figure 6:
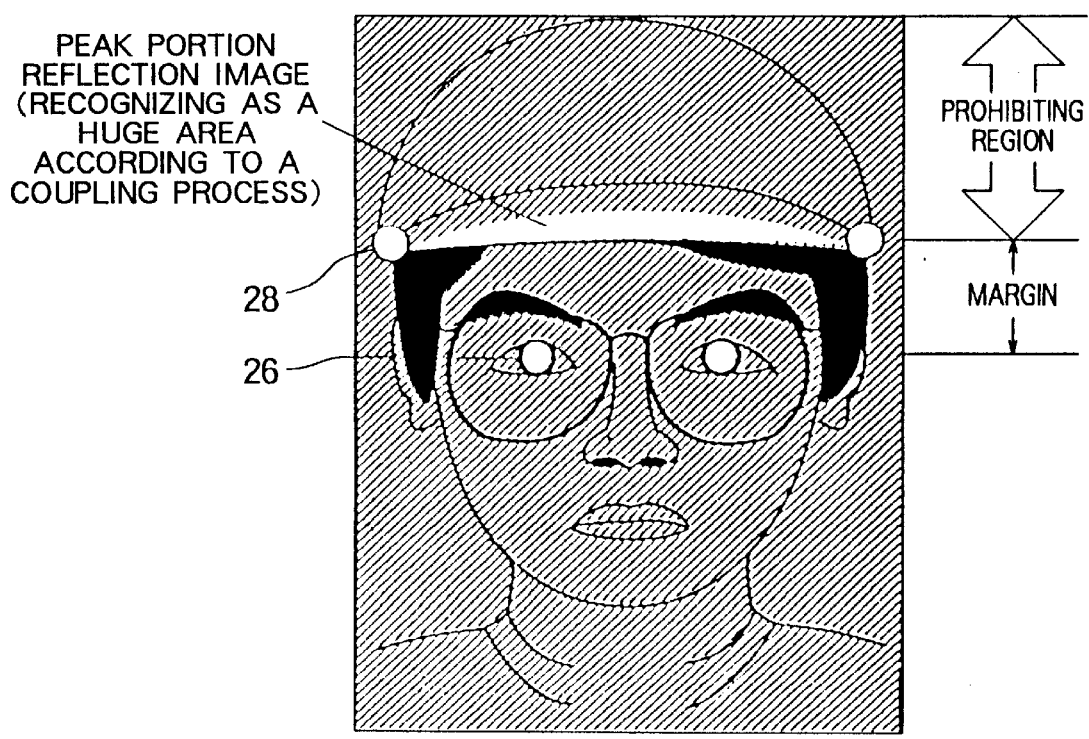
FIG. 6 is an illustrative diagram showing a method of setting a prohibiting region according to a second embodiment of the present invention.

For example, as in FIG. 6 a peak of a helmet is reflected by a LED light, and it is possible that this would be binarized as a lot of contiguous white pixel regions. Then, by selecting two arbitrary points from a group of these regions, because there is the one which fulfills the conditions of a degree of a horizontal or levelness and a distance between both eyes, there is in danger of a false detection of the reflection image at a time of a retinal reflection image extraction of an initial search mode.

Accordingly, recognizing a group of these regions as an extremely large region that is as a huge region, by coupling the regions themselves within the adjacent coupling allowable spaces, and setting an upper face from that position as the prohibiting region, and taking it as an upper limit of the tracking window.

Figure 17:
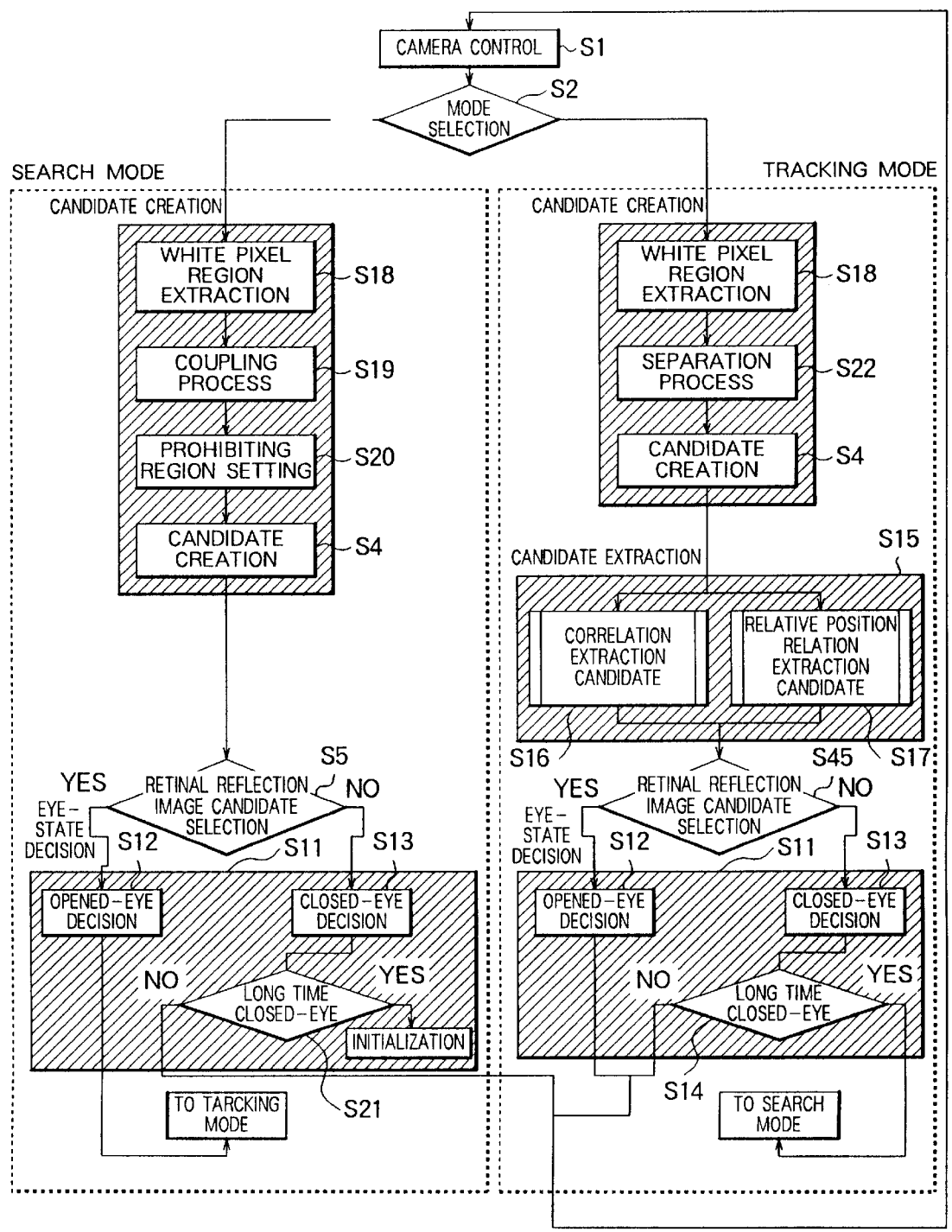
FIG. 17 is a flowchart showing a retinal reflection image tracking algorithm according to the first embodiment of the present invention including the setting of the prohibiting region according to the second embodiment of the present invention and the region separation processing according to the third embodiment of the present invention.

FIG. 17 is a flowchart showing a retinal reflection image tracking algorithm including the prohibiting region setting.

At first, the adjacent regions among the white pixel regions extracted in the white pixel region extraction of the step S18 is recognized as the huge region by coupling them with the coupling process of the step S19, and then the prohibiting region setting is effected at the step S20.

The prohibiting region setting is implemented in the search mode only, and if there is the setting value in the previous time, then it is reset by reflecting that value.

In the tracking mode, the prohibiting region having been set is maintained, and that prohibiting region is removed from the tracking window. Also, the prohibiting region would maintain a certain margin from the retinal reflection image detection position.

However, when a closed eye decision of a long time has been made in the search mode at the step S21, the prohibiting region is initialized and thus released.

Figure 7A:
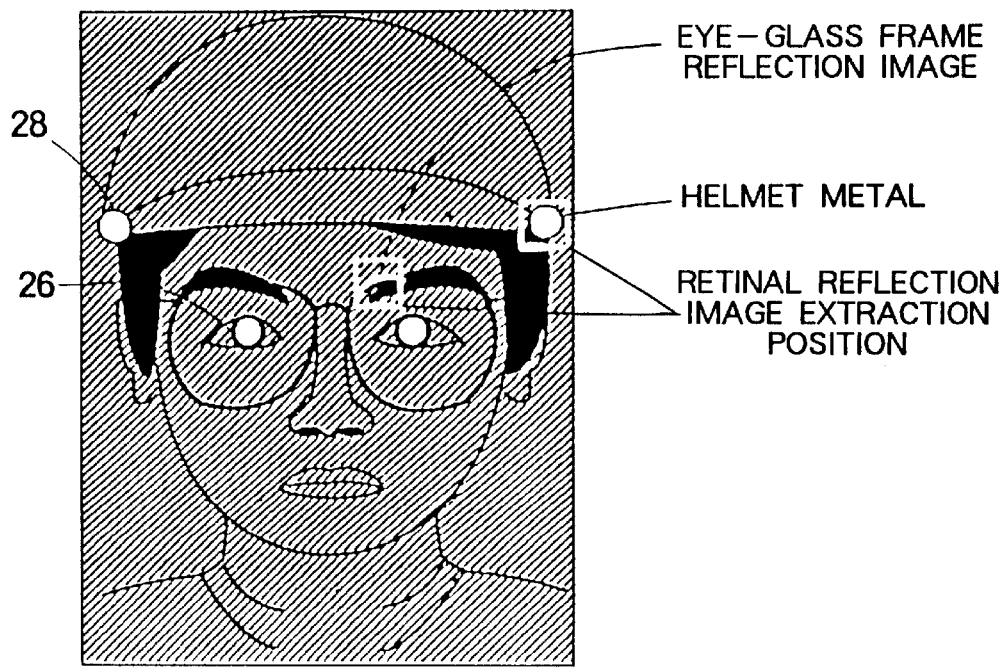
FIGS. 7(a) and 7(b) are illustrative diagrams showing an example of a constraint condition according to the second embodiment of the present invention.
Figure 7B:
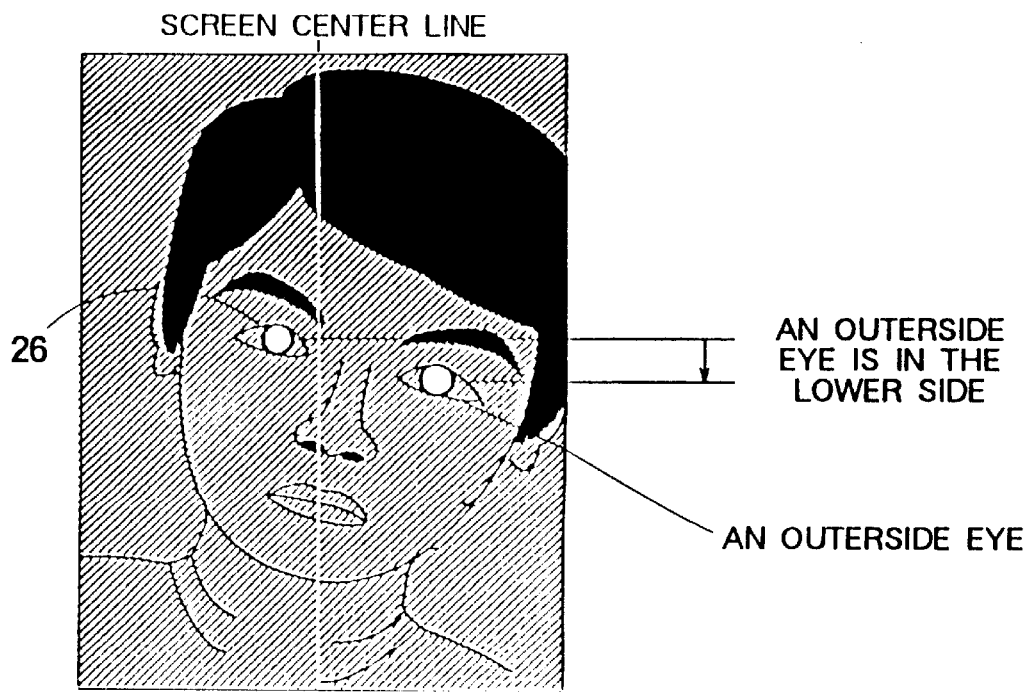

Although an upper part of the face was set as the prohibiting region herein, for example, as shown in FIG. 7(a), since there would be the false detection of the eye glass frame and the helmet metal, it is considered to set the prohibiting region as the constraint condition such as "an outer eye (i.e., an eye more remote from the center line of the screen) exists in the lower part of the face with respect to the center line of the screen", from the eye position relation when the detection subjected person has tilted his/her face as shown in FIG. 7(b).

In the face image processing apparatus according to the second embodiment, since the false detection to the reflection image could be controlled, by removing in advance the regions which would be in danger of making a false detection, the retinal reflection image can be extracted accurately, so that the opened and closed states of the eyes can be decided correctly.

Also, the time of tracking processing can be reduced since a small tracking window could be formed.

THIRD EMBODIMENT

The third embodiment is the one which adds a region separation process (step S22 in FIG. 17) in the retinal reflection image candidate region creation of the tracking mode in the above-mentioned first embodiment. An object of this process is to implement an accurate correlation in the correlation extraction candidate creation (step S16 in FIG. 17), by separating the regions which are adjacent or connected in part.

The region separation process will be described.

This process relates to the candidate creation in the tracking mode, as shown in the flowchart of FIG. 17.

Figure 10:
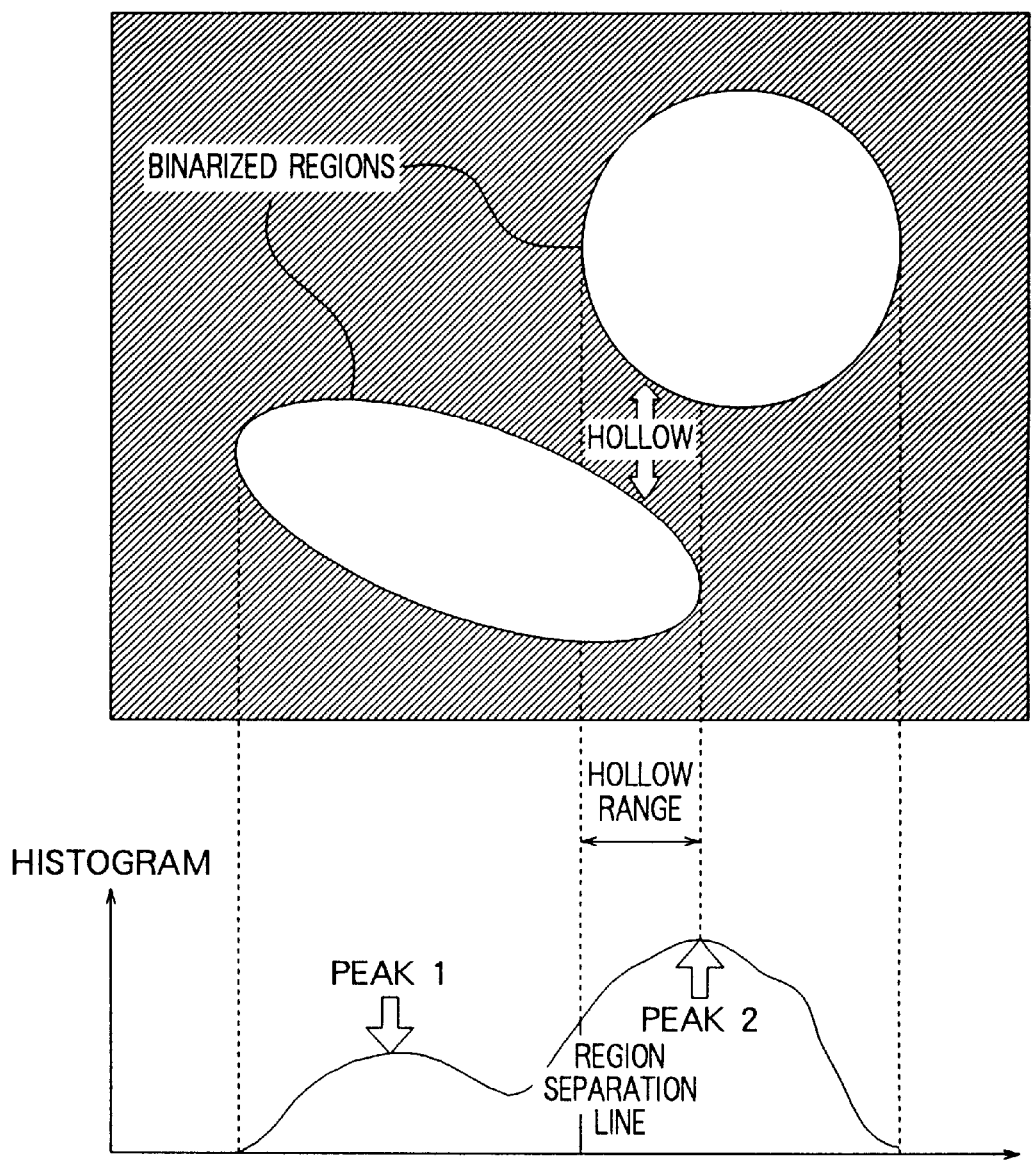
FIG. 10 is an illustrative diagram of a separation of adjacent regions in a region separation process according to a third embodiment of the present invention.

As in FIG. 10, for the binarized regions which are adjacent to each other in a diagonal direction, they can not be separated from each other even if repeating an orthogonal projection and/or a shape histogram in a horizontal or vertical direction.

Therefore, in the third embodiment, by paying attention to a peak which appears on the orthogonal projection, as shown in FIG. 10, it is considered a method of separating the regions in which several high points of the peaks exist, at the low points of the peaks.

Also, it is considered a method of separating them based on a degree of a hollow. A recognition of the hollow is made by such a manner that the values of the orthogonal projection and the difference across the shape histogram are not to be matched, and by using jointly with the peaks previously described, they can be separated.

In the face image processing apparatus according to the third embodiment, since the binarized regions which are adjacent or connected in part can be separated accurately, an correct correlation can be made in the correlation extraction candidate creation, the retinal reflection images can be extracted accurately, thereby the opened and closed states of the eyes can be decided correctly.

FOURTH EMBODIMENT

The face image processing apparatus according to the fourth embodiment is the one which adds a neighboring reflection image extraction process which recognizes the reflection images about the eyes, that are in danger of making a false detection, and continuously tracks until getting lost, independent of the retinal reflection images, in the retinal reflection image region extraction unit 200 of the first embodiment.

An object of this process is to control a false detection to the reflection images which continuously exist in the extremely close positions to the retinal reflection images such as the eye glass lens reflection images of FIG. 8.

The neighboring reflection image extraction process will be described.

A setting of the neighboring reflection image is implemented by canceling the retinal reflection image in the progress of tracking, and then recognizing the candidate which has been canceled as the neighboring reflection image, when the opened-eye state continues for a constant time in the retinal reflection image presently in the progress of tracking, and when the candidate region, which is resembled to the shape features of the retinal reflection image, exists in the up-and-down of the retinal reflection image.

However, when there is no reflection image which would make a false detection as the retinal reflection image, any neighboring reflection image will not be set.

FIG. 18 is a flowchart showing a retinal reflection image tracking algorithm including the neighboring reflection image extraction process. When the retinal reflection image has been canceled at the step S23, for the retinal reflection image which has been selected in the tracking mode retinal reflection image selection of the step S45, the candidate which has been canceled is set as a neighboring reflection image, at the step S24. In this retinal reflection image tracking algorithm, as an attribute of the candidate region, "neighboring reflection image" is added, as shown in the Table 2.

TABLE 2

Correlation Attributes (Fourth Embodiment)

| Attribute | Setting Period of Time |
|---|---|
| Left retinal reflection image | Initial |
| Right retinal reflection image | Initial |
| Left eye neighboring Reflection image | At a time of setting a neighboring reflection image |
| Right eye neighboring Reflection image | At a time of setting a neighboring reflection image |
| Reflection image correlated with Previous screen | Initial |
| Region newly appeared in Present screen but not existed in Previous screen (New Participation) | Every screen |
| Candidates excluded with Overlap Selection Process (Conflict exclusion) | At time of overlap selection process |

After the setting of the neighboring reflection image, as shown in FIG. 18, regardless of a mode selection of the search mode/the tracking mode, tracking the neighboring reflection image by using the retinal reflection image extraction unit of the first embodiment, and if a reflection image is extracted, in the reflection image selection of the step S26 according to the reflection image tracking of the step S25, a false detection is to be prevented by removing a neighboring reflection image from the retinal reflection image selection candidates in advance, before extracting the retinal reflection image in the candidate creation of the search mode (step S4)/the candidate extraction of the tracking mode (step S15).

However, even though an extraction unit of the neighboring reflection image is resembled to the retinal reflection image extraction unit of the first embodiment, with no change, when the neighboring reflection image has been set during the one eye tracking, because it would be the one eye tracking continuously, since the return can not be made even if losing only one screen, a process of track resuming would be added even for the one of the reflection images, only in a case of the neighboring reflection image.

Also when get lost, that position is maintained as a cancel position for the retinal reflection image until a long time decision would be made.

As shown in FIG. 18, no reflection image is extracted in the step S26, and when the closed eye decision continues for a certain time period or the neighboring reflection image lost tracking continues for a certain time period, the neighboring reflection image extraction process will be stopped, in the step S28. At this moment, the above-mentioned cancel position is also to be cleared.

Once it is stopped, the tracking will not be resumed unless the neighboring reflection image setting is made again.

Herein, the neighboring reflection image is used only for removing from the selection candidate at a time of extracting the retinal reflection image, it would be considered to use the neighboring reflection image in the progress of extracting, as a reference position for specifying a position of the retinal reflection image.

In the face image processing apparatus according to the fourth embodiment, the retinal reflection image can be extracted accurately, and the opened and closed states of the eyes can be decided correctly, by controlling a false detection to the reflection image, since the retinal reflection image thereof is recognized and continuously tracked independent of the retinal reflection image, even when the reflection image constantly exists in the position extremely close to the retinal reflection image.

FIFTH EMBODIMENT

The face image processing apparatus according to the fifth embodiment is the one which adds a binarization threshold value control process, depending on the size of the retinal reflection image, in the retinal reflection image candidate region creation of the search mode/the tracking mode of the first embodiment.

The binarization threshold value control process will be described.

Since a size of a retinal reflection image will differ from person to person, and also depending upon a driving style or posture, an environment of surroundings such as pouring of a street light, and a degree of wakefulness of a driver, binarization threshold value control is implemented for the purpose of stably ensuring the appropriate size of a binarized region of the retinal reflection image.

Figure 20:
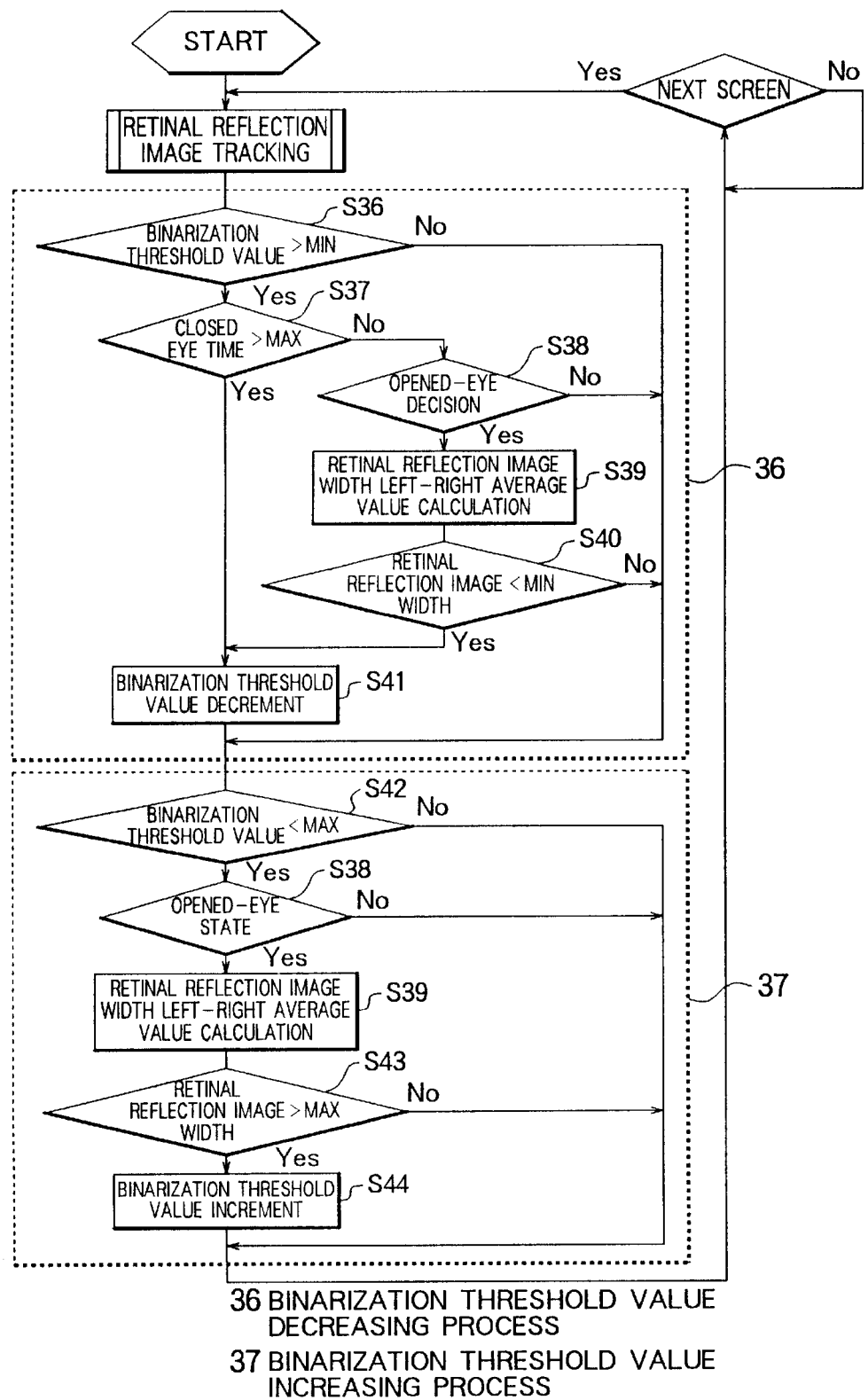
FIG. 20 is a flowchart showing a binarized threshold value control according to a fifth embodiment of the present invention.

For example, in the tracking mode, the binarization threshold value will be increased or decreased in response to an opened- or closed-eye situation and the size of the retinal reflection image binarized region, in accordance with the flowchart of FIG. 20.

A binarization threshold value decreasing process 36 will be described. If the binarization threshold value is larger than the minimum value at the step S36, and the closed eye time is reached to the maximum time period at the step S37, then the binarization threshold value is decreased by one. Also, even if the closed eye time is not reached to the maximum time period at the step S37, when it is an opened-eye decision at the step S38 in the present screen, and when the left and right average value of the retinal reflection image width, which is calculated at the step S39, is smaller than the minimum value at the step S40, then similarly, the binarization threshold value is decreased by one at the step S41. By decreasing the binarization threshold value, a white pixel region to be binarized will become larger, and the retinal reflection image binarization region will not become larger exceedingly, and the size of the retinal reflection image binarization region is kept as a constant.

The binarization threshold value increasing process 37 will be described. If the binarization threshold value is less than the maximum value at the step S42, it is an opened-eye decision at the step S38, and the left and right average value of the retinal reflection image width calculated in the step S39 is larger than the maximum value in the step S43, the binarization threshold value is increased by one. By increasing the binarization threshold value, a white pixel region to be binarized will be smaller, and the retinal reflection image binarized region will not be reduced exceedingly, and the size of the retinal reflection image binarized region is kept as a constant.

In the search mode, when the retinal reflection image can not be found for a certain time period, it is increased/decreased between the lowest threshold value and the highest threshold value with a certain period of time until the retinal reflection image is to be found.

Herein, even though the binarization threshold value control is implemented based on the opened or closed situation of the eyes and the size of the retinal reflection image binarized region, it would be considered to utilize the number of regions of the retinal reflection image candidates and/or the information of the past opened- or closed-eye period of time.

In the face image processing apparatus according to the fifth embodiment, because the binarization threshold value control is implemented so that the size of the retinal reflection image binarized region during the opened eye is to be almost constant, so that the retinal reflection image binarized region can be obtained stably, without depending on an individual difference of the retinal reflection image and a driving situation. As a result, hunting of the opened- or closed-eye decisions and the lost-eye state can be suppressed, enabling accurate decisions of opened- or closed-eye state.

According to the face image processing apparatus of the present invention, the following outstanding advantages will be obtained.

According to the invention as set forth in claim 1, the face image processing apparatus comprises a lighting means for irradiating a face of a person, a photograph means for photographing the face image of the detection subjected person, a binarization means for binarizing a light and shade image of the detection subjected person outputted from the photograph means, a feature extraction means for extracting an image feature from the binarized image outputted from the binarization means, and an eye-state decision means for deciding the opened or closed states of the eyes of the person from an output result of the feature extraction means. The feature extraction means takes the most of the entire binarized regions as the retinal reflection image candidates, and implements the correlation for all these candidates with the previous screen position, so that it can distinguish the retinal reflection images and the reflection images in order to determine the attributes of the retinal reflection images and the reflection images of the candidates in the present screen, according to the previous screen information which they have, irrespective of the surrounding situations of the retinal reflection images such as the opened or closed states and the distribution of the reflection images. As a result, the retinal reflection images can be extracted correctly, and an accurate eye-state decision can be made.

According to the face image processing apparatus of the invention as set forth in claim 2, a prohibiting region setting means sets the binarized regions, which might be mistakenly detected as the retinal reflection images by the retinal reflection image candidate creation means, to be prohibiting regions with respect to the retinal reflection image candidate creation, so that the retinal reflection images can be extracted correctly while preventing the false detection. As a result, an accurate eye-state decision can be made, and the processing time can be reduced.

According to the face image processing apparatus of the invention as set forth in claim 3, the retinal reflection image candidate creation means comprises a left and right retinal reflection images simultaneous search region setting means which sets a tracking window in a range including the left and right retinal reflection images, by extending the tracking window in the up and down directions of the face with the previous screen eye position to be taken as a starting point. As a result, the tracking window can respond to a rapid change in the eye position. Also, a relative positional relation of the left and right as well as a shape feature can be considered simultaneously by treating the left and right eyes as a pair, so that the retinal reflection images can be extracted correctly without regard to a distribution situation of the reflection images, thus enabling an accurate eye-state decision.

According to the face image processing apparatus of the invention as set forth in claim 4, the retinal reflection image candidate creation means comprises a retinal reflection image candidate region separation means which separates the binarized regions which are adjacent or in contact with each other, so that the retinal reflection image correlation extraction means can effect an accurate correlation. Consequently, the retinal reflection images can be extracted correctly to provide an accurate eye-state decision irrespective of the surrounding situations of the retinal reflection images such as the opened-eye or closed-eye states and the movements of the reflection images.

According to the face image processing apparatus of the invention as set forth in claim 5, the retinal reflection image candidate region correlation extraction means comprises a retinal reflection image candidate region correlation overlap selection means which selects, when there is overlapping with the correlations of the retinal reflection image correlation extraction means, one of the overlapped correlations based on a certain reference. Thus, the extracted retinal reflection image is prevented from having double attributes so as to determined uniquely, enabling the correlation to be made accurately. Accordingly, the retinal reflection images can be extracted correctly to provide an accurate eye-state decision irrespective of the surrounding situations of the retinal reflection images such as the opened-eye or closed-eye states and the movements of the reflection images.

According to the face image processing apparatus of the invention as set forth in claim 6, the retinal reflection image candidate region correlation overlap selection means comprises a retinal reflection image candidate region conflict exclusion restoration means for restoring the candidates which have been removed in an overlap selection process by the retinal reflection image correlation extraction means.

The candidates which should be correlated will not be discarded, and accurately correlated again by the retinal reflection image candidate region conflict exclusion restoration means, so that the retinal reflection images can be extracted correctly irrespective of the surrounding situations of the retinal reflection images such as the opened- or closed-eye states and the movements of the reflection images, thus ensuring an accurate eye-state decision.

According to the face image processing apparatus of the invention as set forth in claim 7, a retinal reflection image decision means is provided for deciding whether or not the binarized regions being now tracked are to be the retinal reflection images. With the provision of such means, even if the initial extraction was false, it is abolished and then the retinal reflection image extraction can be re-started, thereby ensuring an accurate eye-state decision.

According to the face image processing apparatus of the invention as set forth in claim 8, a neighboring reflection image extraction means is provided for recognizing as the retinal reflection image neighboring reflection images the binarized regions which has been decided as the reflection images by the retinal reflection image deciding means and for implementing the continuous tracking, independent of the retinal reflection images, even though the reflection images constantly exist in the positions which are extremely close to the retinal reflection images, without making a false detection of the same regions again. As a consequence, the retinal reflection image extraction can made correctly, and an accurate eye-state decision can be made.

According to the face image processing apparatus of the invention as set forth in claim 9, the relative position relation extraction means is provided independent of the retinal reflection image correlation extraction means, so that it complements the retinal reflection image correlation extraction means so as to correctly extract the retinal reflection image without losing the track of the retinal reflection images, thus ensuring an most accurate eye-state decision.

According to the face image processing apparatus of the invention as set forth in claim 10, the sizes of the retinal reflection image binarized regions in the state of open eyes can be maintained constant through the binarization threshold value control, stable retinal reflection image binarized regions can be obtained without depending on the individual differences in the retinal reflection images, the environmental situations such as driving conditions, and the like. As a result, hunting of the opened-eye and closed-eye states and the lost-eye state can be suppressed, thus enabling the opened or closed states of the eyes to be decided correctly.

What is claimed is:

1. A face image processing apparatus comprising:

a retinal reflection image creation optical means for creating retinal reflection images in eye balls of a person;

an image input means for inputting a face image of said person;

a binarization means for binarizing a light and shade image obtained by said image input means;

a retinal reflection image candidate creation means for defining retinal reflection image candidate regions in a binarized image;

a retinal reflection image region extraction means for extracting a retinal reflection image region from a group of said retinal reflection image candidate regions; and an eye-state decision means for determining whether an eye is in an opened or a closed state according to said retinal reflection image region extracted by said retinal reflection image region extraction means;

wherein, said retinal reflection image region extraction means comprises a retinal reflection image candidate region correlation extraction means for correlating a retinal reflection image candidate region of a present time with a retinal reflection image candidate region of a predetermined previous time.

2. A face image processing apparatus according to claim 1, wherein said retinal reflection image candidate creation means comprises a prohibiting region setting means for preventing a creation of a retinal reflection image candidate within a binarized image.

3. A face image processing apparatus according to claim 1, wherein said retinal reflection image candidate creation means comprises a left and right retinal reflection images simultaneous search region setting means for setting a region, for which a retinal reflection image candidate creation is implemented, to a range including the left and right retinal reflection images.

4. A face image processing apparatus according to claim 1, wherein said retinal reflection image candidate creation means comprises a retinal reflection image candidate region separation means for separating said retinal reflection image candidate regions neighboring or contacting with each other.

5. A face image processing apparatus according to claim 1, wherein said retinal reflection image candidate region correlation extraction means comprises a retinal reflection image candidate region correlation overlap selection means which selects, if a plurality of retinal reflection image candidate regions of the present time are correlated in an overlapping manner with the same retinal reflection image candidate regions of the predetermined previous time, any one of said retinal reflection image candidate regions of the present time.

6. A face image processing apparatus according to claim 5, wherein said retinal reflection image candidate region correlation overlap selection means comprises a retinal reflection image candidate region conflict exclusion restoration means for renewing and correlating the retinal reflection image candidate regions of the present time, which have been excluded from the correlation with the same retinal reflection image candidate regions of the predetermined previous time effected by said retinal reflection image candidate region correlation overlap selection means, with other retinal reflection image candidate regions of the predetermined previous time.

7. A face image processing apparatus according to claim 1, wherein said retinal reflection image candidate region extraction means comprises a retinal reflection image decision means for evaluating the retinal reflection image candidate regions which are being extracted as the retinal reflection image at the present time, and for abolishing the retinal reflection image candidate regions which are being extracted as the retinal reflection image at the present time, in based upon a result of the evaluation.

8. A face image processing apparatus according to claim 7, wherein said retinal reflection image decision means further comprises a non-retinal reflection image region extraction means for continuously extracting, independent of the retinal reflection image regions, the retinal reflection image candidate regions which have been abolished as the non-retinal reflection images by said retinal reflection image decision means.

9. A face image processing apparatus according to claim 1, wherein said retinal reflection image extraction means comprises:

a retinal reflection image relative position relation extraction means for extracting, to the left and right simultaneously, the retinal reflection image candidate regions of the present time as the left and right retinal reflection images; and a retinal reflection image region selection means for selecting one of two kids of retinal reflection image regions extracted by said retinal reflection image canadidate region correlation extraction means and said retinal reflection image relative position relation extraction means.

10. A face image processing apparatus according to claim 1, wherein said binarization means comprises a binarized threshold value control means for controlling a binarized threshold value corresponding to a size of a retinal reflection image.

* * * * *